United States Patent [19]

Cavalla et al.

[11] Patent Number: 5,922,751
[45] Date of Patent: Jul. 13, 1999

[54] ARYL PYRAZOLE COMPOUND FOR INHIBITING PHOSPHODIESTERASE IV AND METHODS OF USING SAME

[75] Inventors: David John Cavalla, Cambridge, United Kingdom; Mark Chasin, Manalapan, N.J.; Lloyd J. Dolby, Eugene, Oreg.; Richard William Frith, Cambridge, United Kingdom

[73] Assignee: Euro-Celtique, S.A., Luxembourg, Luxembourg

[21] Appl. No.: 08/782,502

[22] Filed: Jan. 10, 1997

Related U.S. Application Data

[63] Continuation of application No. 08/486,184, Jun. 7, 1995, abandoned, which is a continuation-in-part of application No. 08/265,641, Jun. 24, 1994, abandoned.

[51] Int. Cl.⁶ .......... A61K 31/415; A61K 31/41; A61K 31/42; A61K 31/425

[52] U.S. Cl. .......... 514/407; 514/404; 514/406; 514/359; 514/383; 514/384; 514/389; 548/366.1; 548/370.4; 548/371.4; 548/371.7; 548/372.5; 548/374.1; 548/376.1; 548/255; 548/262.2; 548/264.8; 548/317.1; 548/318.5; 548/331.5; 548/333.1; 548/333.5; 548/343.1; 548/334.5; 548/342.5; 548/343.5; 548/346.1

[58] Field of Search .......... 548/370.4, 371.7, 548/372.5, 374.1, 371.4, 376.1, 366.1; 514/404, 406, 407

[56] References Cited

U.S. PATENT DOCUMENTS

| Re. 31,429 | 10/1983 | Tull et al. | 544/277 |
|---|---|---|---|
| 2,320,654 | 6/1943 | Riester | 95/7 |
| 2,691,654 | 10/1954 | Hitchings | 260/247.5 |
| 2,844,577 | 7/1958 | Acker | 260/254 |
| 2,903,455 | 9/1959 | Strong et al. | 260/252 |
| 2,956,998 | 10/1960 | Baizer | 260/252 |
| 2,957,875 | 10/1960 | Lyttle et al. | 260/252 |
| 2,966,488 | 12/1960 | Shive et al. | 260/252 |
| 3,079,378 | 2/1963 | Schroeder | 260/211.5 |
| 3,129,225 | 4/1964 | Shapiro | 260/247.2 |
| 3,135,753 | 6/1964 | Hitchings | 540/265 |
| 3,136,771 | 6/1964 | Liechti et al. | 260/296 |
| 3,215,696 | 11/1965 | Denayer | 260/252 |
| 3,225,046 | 12/1965 | Zwahlen | 260/252 |
| 3,262,929 | 7/1966 | Okubu et al. | 260/240 |
| 3,470,164 | 9/1969 | Takamatsu | 260/240 |
| 3,491,091 | 1/1970 | Berger | 260/240 |
| 3,491,106 | 1/1970 | Freyermuth | 260/304 |
| 3,494,919 | 2/1970 | Collins et al. | 260/240 |
| 3,516,997 | 6/1970 | Takano et al. | 260/243 |
| 3,541,100 | 11/1970 | Ramirez et al. | 260/286 |
| 3,551,554 | 12/1970 | Herschler | 424/7 |
| 3,574,218 | 4/1971 | Hideg et al. | 260/293.4 |
| 3,586,670 | 6/1971 | Brenneisen | 260/240 |
| 3,590,029 | 6/1971 | Koch | 260/211.5 |
| 3,626,018 | 12/1971 | Taylor | 260/670 |
| 3,636,039 | 1/1972 | Gruenman et al. | 260/309.7 |
| 3,647,812 | 3/1972 | Smith | 260/304 |
| 3,658,799 | 4/1972 | Eardley | 260/243 C |
| 3,666,769 | 5/1972 | Jones | 260/304 |
| 3,669,979 | 6/1972 | Freyermuth | 260/304 |

(List continued on next page.)

FOREIGN PATENT DOCUMENTS

| 994351 | 8/1976 | Canada | 260/393.2 |
|---|---|---|---|
| 0178413 | 4/1986 | European Pat. Off. | C07D 235/18 |
| 0191313 | 8/1986 | European Pat. Off. | C07D 473/22 |
| 0203721 | 12/1986 | European Pat. Off. | C07D 473/06 |
| 0256692 | 2/1988 | European Pat. Off. | C07D 473/22 |
| 0258191 | 3/1988 | European Pat. Off. | C07D 473/06 |
| 0343643 | 11/1989 | European Pat. Off. | A61K 31/41 |
| 360701 | 3/1990 | European Pat. Off. | |
| 0369744 | 5/1990 | European Pat. Off. | C07D 473/06 |
| 0386683 | 9/1990 | European Pat. Off. | C07D 473/04 |
| 0389282 | 9/1990 | European Pat. Off. | C07D 473/06 |
| 0018136 | 10/1990 | European Pat. Off. | C07D 473/22 |
| 0400799 | 12/1990 | European Pat. Off. | C07D 239/36 |
| 0417790 | 3/1991 | European Pat. Off. | C07D 487/14 |
| 0435811 | 7/1991 | European Pat. Off. | C07D 473/04 |
| 0463756 | 1/1992 | European Pat. Off. | C07D 487/04 |
| 0470805 | 2/1992 | European Pat. Off. | C07C 271/60 |
| 0497564 | 8/1992 | European Pat. Off. | C07C 235/36 |
| 0511865 | 11/1992 | European Pat. Off. | C07D 231/08 |
| 0536713 | 4/1993 | European Pat. Off. | C07D 263/34 |
| 0590919 | 4/1994 | European Pat. Off. | C07D 473/06 |
| 0619316 | 10/1994 | European Pat. Off. | C07D 473/04 |
| 0623607 | 11/1994 | European Pat. Off. | C07D 307/80 |
| 0645389 | 3/1995 | European Pat. Off. | C07D 471/04 |
| 0671389 | 9/1995 | European Pat. Off. | C07D 207/08 |

(List continued on next page.)

OTHER PUBLICATIONS

Ronald E. Weishaar, et al., Subclasses of Cyclic GMP–Specific phosphodiesterase and their role in regulating the effects of atrial natriuretic factor, Dept. of Pharmacology, Parke–Davis Pharmaceutical Research Division, Warner–Lambert Co. Hypertension, vol. 15, No. 5, May, 1990, p. 528.

"Structure–Activity Relationships in a Series of 6–Thioxanthines with Bronchodilator and Coronary Dilator Properties", A.K. Armitrage, Janet Boswood and B.J. Large, Brit. J. Pharma. 1961, 17:196–207.

"The Synthesis of Some 6 Thioxanthines", K.R.H. Wooldrige and R. Slack, J. Chem. Soc., 1962, Annex IV:1863–1868.

Chemical Abstracts, vol. 85, No. 1 (Jul. 9, 1976) 5692s (Enoki).

(List continued on next page.)

Primary Examiner—Jose' G. Dees
Assistant Examiner—Laura L. Stockton
Attorney, Agent, or Firm—Davidson, Davidson & Kappel, LLC

[57] ABSTRACT

Novel compounds which are effective PDE IV inhibitors are disclosed The compounds possess similar or improved PDE IV inhibition as compared to rolipram, with improved selectivity with regard to, e.g., PDE III inhibition. Preferred compounds are 3-(3-cyclopentyloxy-4-methoxy-benzylamino)-4-hydroxymethyl pyrazole and 3-(3-cyclopentyloxy-4-methoxybenzylamino)-4-methoxymethylpyrazole.

24 Claims, No Drawings

U.S. PATENT DOCUMENTS

| | | | |
|---|---|---|---|
| 3,674,781 | 7/1972 | Schinzel et al. | 260/240 |
| 3,681,328 | 8/1972 | Kurita | 260/243 C |
| 3,686,238 | 8/1972 | Zaffaroni | 260/399 |
| 3,706,834 | 12/1972 | Scheilenbaum et al. | 424/272 |
| 3,923,833 | 12/1975 | Gruenmann et al. | 260/340.5 |
| 3,962,452 | 6/1976 | Evans et al. | 424/272 |
| 4,020,165 | 4/1977 | Hubbard | 514/367 |
| 4,025,636 | 5/1977 | Dunwell et al. | 424/269 |
| 4,025,637 | 5/1977 | Dunwell | 424/272 |
| 4,107,306 | 8/1978 | Voorhees | 424/248.51 |
| 4,167,628 | 9/1979 | Kormany | 542/454 |
| 4,233,303 | 11/1980 | Bergstrand et al. | 424/253 |
| 4,241,063 | 12/1980 | Naito et al. | 424/253 |
| 4,241,168 | 12/1980 | Arai | 430/503 |
| 4,308,278 | 12/1981 | Schneider et al. | 424/273 |
| 4,361,699 | 11/1982 | Rasmusson et al. | 544/277 |
| 4,407,802 | 10/1983 | Graham et al. | 424/253 |
| 4,416,892 | 11/1983 | Dawson | 424/272 |
| 4,454,138 | 6/1984 | Goring | 424/253 |
| 4,469,698 | 9/1984 | Phillppossian et al. | 424/253 |
| 4,616,020 | 10/1986 | Furrer et al. | 514/264 |
| 4,652,654 | 3/1987 | Verga et al. | 548/217 |
| 4,684,656 | 8/1987 | Atwal | 514/274 |
| 4,684,728 | 8/1987 | Möhring | 544/182 |
| 4,710,503 | 12/1987 | Hofer | 514/263 |
| 4,732,978 | 3/1988 | Kreft et al. | 546/152 |
| 4,755,517 | 7/1988 | Bruns et al. | 514/263 |
| 4,757,124 | 7/1988 | Koyanagi | 526/62 |
| 4,769,377 | 9/1988 | Snyder et al. | 514/263 |
| 4,770,990 | 9/1988 | Nakamura | 430/564 |
| 4,803,216 | 2/1989 | Appleton et al. | 514/407 |
| 4,810,719 | 3/1989 | Appleton et al. | 514/406 |
| 4,826,868 | 5/1989 | Wachter et al. | 514/407 |
| 4,831,152 | 5/1989 | Itoh et al. | 548/224 |
| 4,851,321 | 7/1989 | Takagi | 430/264 |
| 4,874,869 | 10/1989 | Ueda et al. | 548/309 |
| 4,883,801 | 11/1989 | Nathanson | 514/263 |
| 4,910,211 | 3/1990 | Imamura et al. | 514/367 |
| 4,918,074 | 4/1990 | Tsuda et al. | 514/258 |
| 4,925,847 | 5/1990 | Hofer | 514/263 |
| 4,965,169 | 10/1990 | Hirano | 430/264 |
| 4,971,972 | 11/1990 | Doll et al. | 514/265 |
| 4,981,857 | 1/1991 | Daluge | 574/263 |
| 4,994,363 | 2/1991 | Koya et al. | 430/564 |
| 5,010,081 | 4/1991 | Hofer | 514/263 |
| 5,047,411 | 9/1991 | Takasugi et al. | 514/300 |
| 5,057,517 | 10/1991 | Johnston et al. | 514/254 |
| 5,068,236 | 11/1991 | Suzuki et al. | 514/263 |
| 5,091,431 | 2/1992 | Tulshian et al. | 514/262 |
| 5,098,464 | 3/1992 | Barton et al. | 71/92 |
| 5,110,818 | 5/1992 | Allgeier | 514/261 |
| 5,114,835 | 5/1992 | Sakaoue | 430/393 |
| 5,116,717 | 5/1992 | Matsushita | 430/264 |
| 5,117,830 | 6/1992 | McAfee et al. | 128/654 |
| 5,139,921 | 8/1992 | Takagi et al. | 430/264 |
| 5,177,074 | 1/1993 | Allen et al. | 514/234 |
| 5,177,085 | 1/1993 | Naef | 514/307 |
| 5,190,942 | 3/1993 | Poss | 514/235.8 |
| 5,191,084 | 3/1993 | Bagli et al. | 546/279 |
| 5,206,255 | 4/1993 | Ubasawa et al. | 514/374 |
| 5,264,589 | 11/1993 | Corey | 548/51 |
| 5,270,206 | 12/1993 | Saccomano | 435/280 |
| 5,288,896 | 2/1994 | Capiris et al. | 560/27 |
| 5,290,782 | 3/1994 | Suzuki et al. | 514/263 |
| 5,322,847 | 6/1994 | Marfat et al. | 514/303 |
| 5,342,835 | 8/1994 | Pepin et al. | 514/227.5 |
| 5,424,432 | 6/1995 | Fredenburgh et al. | 546/118 |
| 5,434,150 | 7/1995 | Austel et al. | 514/228.5 |
| 5,449,686 | 9/1995 | Christensen, IV | 514/330 |
| 5,451,596 | 9/1995 | Ullrich | 514/375 |
| 5,496,853 | 3/1996 | Shiota et al. | 514/469 |
| 5,602,157 | 2/1997 | Christensen, IV | 514/362 |
| 5,602,173 | 2/1997 | Christensen, IV | 514/475 |
| 5,631,260 | 5/1997 | Belardinelli et al. | 514/263 |

FOREIGN PATENT DOCUMENTS

| | | | |
|---|---|---|---|
| 0675124 | 10/1995 | European Pat. Off. | C07D 473/30 |
| 0685474 | 12/1995 | European Pat. Off. | C07D 307/80 |
| 0685479 | 12/1995 | European Pat. Off. | C07D 409/14 |
| 0728759 | 8/1996 | European Pat. Off. | C07D 487/04 |
| 0731099 | 9/1996 | European Pat. Off. | C07D 307/82 |
| 0779291 | 6/1997 | European Pat. Off. | C07D 405/04 |
| 835818 | 2/1961 | France . | |
| 1548252 | 12/1968 | France . | |
| 2104932 | 6/1972 | France . | |
| 2008464 | 9/1970 | Germany | C07D 52/60 |
| 2314676 | 10/1973 | Germany | C07D 91/44 |
| 2346034 | 4/1974 | Germany . | |
| 5154587 | 5/1976 | Japan | C07D 473/02 |
| 5721375 | 2/1982 | Japan | C07D 235/18 |
| 559056 | 3/1993 | Japan | C07D 473/22 |
| 6211856 | 8/1994 | Japan | C07D 473/06 |
| 7118247 | 5/1995 | Japan | C07D 277/46 |
| 717952 | 7/1995 | Japan | C07D 233/70 |
| 8113567 | 5/1996 | Japan | C07D 263/56 |
| 215948 | 10/1989 | New Zealand | C07D 473/00 |
| 1077689 | 8/1967 | United Kingdom | C07D 57/38 |
| 1260793 | 1/1972 | United Kingdom | C07C 85/48 |
| 1498705 | 1/1978 | United Kingdom | C07D 207/26 |
| 1561005 | 2/1980 | United Kingdom | C07D 473/28 |
| 2041359 | 9/1980 | United Kingdom | C07D 473/34 |
| 1580782 | 12/1980 | United Kingdom | C07D 473/06 |
| 2283488 | 5/1995 | United Kingdom | C07D 217/12 |
| 8601724 | 3/1986 | WIPO | A61L 9/04 |
| 8706576 | 4/1986 | WIPO | C07C 47/11 |
| 9631487 | 10/1986 | WIPO | C07D 233/70 |
| 9100858 | 1/1991 | WIPO | C07D 233/60 |
| 9200968 | 1/1992 | WIPO | C07D 239/02 |
| 9205175 | 4/1992 | WIPO | C07D 473/06 |
| 9207567 | 5/1992 | WIPO | A61K 31/535 |
| 9219594 | 11/1992 | WIPO | C07D 207/26 |
| 9307111 | 4/1993 | WIPO | C07C 49/753 |
| 9307141 | 4/1993 | WIPO | C07D 401/06 |
| 9314081 | 7/1993 | WIPO | C07D 401/04 |
| 9314082 | 7/1993 | WIPO | C07D 401/04 |
| 9315044 | 8/1993 | WIPO | C07C 237/22 |
| 9315045 | 8/1993 | WIPO | C07C 237/22 |
| 9318024 | 9/1993 | WIPO | C07D 335/02 |
| 9319747 | 10/1993 | WIPO | A61K 31/227 |
| 9319749 | 10/1993 | WIPO | A61K 31/275 |
| 9319750 | 10/1993 | WIPO | A61K 31/275 |
| 9319751 | 10/1993 | WIPO | A61K 31/275 |
| 9322287 | 11/1993 | WIPO . | |
| 9325517 | 12/1993 | WIPO | C07C 233/75 |
| 9402465 | 2/1994 | WIPO | C07D 213/75 |
| 9410118 | 5/1994 | WIPO | C07C 43/235 |
| 9412461 | 6/1994 | WIPO . | |
| 9414742 | 7/1994 | WIPO | C07C 43/253 |
| 9414800 | 7/1994 | WIPO | C07D 405/06 |
| 9420446 | 9/1994 | WIPO | C07C 43/235 |
| 9420455 | 9/1994 | WIPO | C07C 255/36 |
| 9420460 | 9/1994 | WIPO | C07D 207/02 |
| 9422859 | 10/1994 | WIPO | C07D 471/04 |
| 9425437 | 11/1994 | WIPO | C07D 211/22 |
| 9500139 | 1/1995 | WIPO | A61K 31/275 |
| 9501338 | 1/1995 | WIPO | C07D 213/75 |
| 9503297 | 2/1995 | WIPO | C07D 401/04 |
| 9503794 | 2/1995 | WIPO | A61K 31/275 |
| 9504045 | 2/1995 | WIPO | C07D 213/75 |
| 9504046 | 2/1995 | WIPO | C07D 213/75 |
| 9508534 | 3/1995 | WIPO | C07D 207/16 |
| 9509623 | 4/1995 | WIPO | A61K 31/275 |
| 9509624 | 4/1995 | WIPO | A61K 31/275 |
| 9509627 | 4/1995 | WIPO | A61K 31/375 |
| 9509836 | 4/1995 | WIPO | C07D 255/46 |
| 9509837 | 4/1995 | WIPO | C07C 255/46 |

| | | | |
|---|---|---|---|
| 9604253 | 5/1995 | WIPO | C07D 239/10 |
| 9514667 | 6/1995 | WIPO | C07D 209/34 |
| 9517386 | 6/1995 | WIPO | C07D 213/30 |
| 9517392 | 6/1995 | WIPO | C07D 261/12 |
| 9517399 | 6/1995 | WIPO | C07D 413/10 |
| 9522520 | 8/1995 | WIPO | C07C 235/42 |
| 9523148 | 8/1995 | WIPO | C07D 473/06 |
| 9527692 | 10/1995 | WIPO | C07C 43/23 |
| 9535281 | 12/1995 | WIPO | C07D 213/30 |
| 9535282 | 12/1995 | WIPO | C07D 213/30 |
| 9535283 | 12/1995 | WIPO | C07D 213/30 |
| 9535284 | 12/1995 | WIPO | C07D 213/30 |
| 9535285 | 12/1995 | WIPO | C07D 213/30 |
| 9600215 | 1/1996 | WIPO | C07D 213/53 |
| 9603396 | 2/1996 | WIPO | C07D 307/79 |
| 9603399 | 2/1996 | WIPO | C07D 401/12 |
| 9612720 | 5/1996 | WIPO | C07D 471/04 |
| 9620157 | 7/1996 | WIPO | C07C 69/76 |
| 9620158 | 7/1996 | WIPO | C07C 69/76 |
| 9620174 | 7/1996 | WIPO | C07D 213/02 |
| 9620175 | 7/1996 | WIPO | C07D 213/30 |
| 9624350 | 8/1996 | WIPO | A61K 31/42 |
| 9631476 | 10/1996 | WIPO | C07D 213/75 |
| 9631485 | 10/1996 | WIPO | C07D 233/32 |
| 9631486 | 10/1996 | WIPO | C07D 233/32 |
| 9628430 | 11/1996 | WIPO | C07D 239/88 |
| 963624 | 11/1996 | WIPO | C07D 307/80 |
| 9636595 | 11/1996 | WIPO | C07C 311/29 |
| 9636596 | 11/1996 | WIPO | C07C 311/29 |
| 9636611 | 11/1996 | WIPO | C07D 215/58 |
| 9636625 | 11/1996 | WIPO | C07D 307/94 |
| 9636626 | 11/1996 | WIPO | C07D 307/94 |
| 9636638 | 11/1996 | WIPO | C07D 473/06 |
| 9638150 | 12/1996 | WIPO | A61K 31/505 |
| 9703070 | 1/1997 | WIPO | C07D 403/12 |
| 9703967 | 2/1997 | WIPO | C07D 213/81 |
| 9712887 | 4/1997 | WIPO | C07D 473/00 |
| 9712888 | 4/1997 | WIPO | C07D 473/00 |
| 9720833 | 6/1997 | WIPO | C07D 307/80 |
| 9722585 | 6/1997 | WIPO | C07D 213/30 |
| 9722586 | 6/1997 | WIPO | C07D 213/30 |
| 9723457 | 7/1997 | WIPO | C07D 209/48 |
| 9723460 | 7/1997 | WIPO | C07D 213/30 |
| 9723461 | 7/1997 | WIPO | C07D 213/40 |
| 9724334 | 7/1997 | WIPO | C07D 235/08 |
| 9725312 | 7/1997 | WIPO | C07D 207/26 |
| 9728143 | 8/1997 | WIPO | C07D 307/79 |
| 9728144 | 8/1997 | WIPO | C07D 307/79 |
| 9728145 | 8/1997 | WIPO | C07D 307/79 |
| 9728146 | 8/1997 | WIPO | C07D 307/79 |
| 9728147 | 8/1997 | WIPO | C07C 307/79 |
| 9728148 | 8/1997 | WIPO | C07D 307/79 |
| 9728155 | 8/1997 | WIPO | C07D 405/06 |

OTHER PUBLICATIONS

Chemical Abstracts, vol. 84, No. 25 (Jun. 21, 1976) 180299v (Enoki).

Chemical Abstracts, vol. 86, No. 7 (Feb. 14, 1977) 43746r (Aida).

Isomura et al., "Studies on the synthesis and anti–inflammatory activity of 2,6–Di–tert–butylphenols with a heterocyclic group at the 4–position.I", vol. 31, No. 9, pp. 3168–3178 (1983).

Chemical Abstracts 103: 37354, 1985 (Nagarajan).

Chemical Abstracts 116: 255335, 1992 (Bender).

Itaya, *Tetrahedron Letters*, vol. 23, No. 21 (1982), pp. 2203–2204.

Reitz, *Journal of Organic Chemistry*, vol. 55, No. 22 (Oct. 26, 1990), pp. 5761–5766.

Chemical Abstracts 88: 51054, 1977 (Ninomiya).

Chemical Abstracts, vol. 82 (19) May 12, 1975, Abstract #125358x (Kazimierezuk).

Chemical Abstracts 114: 246982, 1990 (Naruto).

"Controlled Interaction between Nucleic Acid Bases. Intramolecular Stacking Interactions between Two Adenine Rings", Nelson J. Leonard, et al.; Journal of the American Chemical Society, 95:12, Jun. 13, 1973, pp. 4010–4016.

Chemical Abstracts 92: 6207, 1977 (Pirisino).

Ronald E. Weishaar, et al., Multiple molecular forms of cyclic nucleotide phosphodiesterase in cardiac and smooth muscle and in platelets, Biochemical Pharmacology, vol. 35, No. 5., pp. 787–800, 1986.

G.T. Rogers and T.L.V. Ulbricht, Synthesis of 3–Methylisoguanine (6–amino–3–methylpurin–2(3H)–one), J. Chem. Soc. (C), pp. 2364–2366, 1971.

Chemical Abstracts 116:173873 (1979) Girshovich.

J. A. Montgomery, et al., "Synthesis of Potential Anticancer Agents. XIX. 2–Substituted $N^6$–Alkyladenines" (1959) J.A.C.S. vol 81, pp. 3963–3967.

Chemical Abstracts 53:6243, (1957) Elion.

T. Fuji, et al. "3–Substituted Adenines. In Vitro Enzyme Inhibition and Antiviral Activity", (1979) Journal of Medicinal Chemistry, vol. 22, No. 2, pp. 126–129.

Burger, Ed. "Medicinal Chemistry" 2d ed. pp. 42–43, Interscience, New York, New York (1960).

Derwent Abstract of JP 1200246, published Aug. 11, 1989.

Derwent Abstract of JP 1245256, published Sep. 29, 1989.

Derwent Abstract of JP 1231049, published Sep. 14, 1989.

Derwent Abstract of JP 1229251, published Sep. 12, 1989.

Derwent Abstract of JP 1225951, published Sep. 8, 1989.

Derwent Abstract of JP 1224756, published Sep. 7, 1989.

Derwent Abstract of JP 1224755, published Sep. 7, 1989.

Derwent Abstract of JP 1219748, published Sep. 1, 1989.

Derwent Abstract of JP 1216353, published Aug. 20, 1989.

Derwent Abstract of JP 1214845, published Aug. 29, 1989.

Derwent Abstract of JP 1093733, published Apr. 12, 1989.

Derwent Abstract of JP 63271246, published Nov. 9, 1988.

Derwent Abstract of JP 58111034, published Jul. 1, 1983.

Derwent Abstract of DE 144519 (1964).

CA Select: "Anti–Inflammatory Agents & Arthritis" Issue 7, 1996, p. 26, 124:1467542.

Abstract of PCT Gazette—Section I, No. 26/19 of WO 96/16657, 1996.

Abstract of JP 6–192244 (1 page), 1994.

CA of "1–Pharmacology", vol. 106, 1987, p. 61, 106:27814n.

CA Selects: "Allergy & Antiallergic Agents", Issue 5, 1996, pp. 17 and 19, 124:85064a and 124:87030k.

CA Selects: "Allergy & Antiallergic Agents", Issue 21, 1995, p. 13, 123:169611u.

CA Selects: Anti–Inflammatory Agents & Arthritis, Issue 23, 1995, pp. 17 and 23, 123:228202m.

CA Selects: "Anti–Inflammatory Agents & Arthritis", Issue 25, 1996, (1 page), 125:275430k.

CA 171494, 171495 and KG–2683 of Annual Drug Data Report, 1991 (1 sheet).

Derwent Abstract of DE4309969, 1993.

Chemical Abstract 82:132795, 1975.

Chemical Abstract 84:150660, 1976.

Chemical Abstract 114:42729, 1991.

Chemical Abstract 116:235266, 1992.

Chemical Abstract 122:290715, 1995.

ARYL PYRAZOLE COMPOUND FOR INHIBITING PHOSPHODIESTERASE IV AND METHODS OF USING SAME

This application is a continuation of application Ser. No. 08/486,184 filed Jun. 7, 1995, which application is now abandoned, which is a continuation-in-part of U.S. Ser. No. 08/265,641, filed Jun. 24, 1994, now abandoned, both of which are hereby incorporated by reference.

BACKGROUND OF THE INVENTION

Asthma is a complex disease involving the concerted actions of multiple inflammatory and immune cells, spasmogens, inflammatory mediators, cytokines and growth factors. In recent practice there have been four major classes of compounds used in the treatment of asthma, namely bronchodilators (e.g., β-adrenoceptor agonists), anti-inflammatory agents (e.g., corticosteroids), prophylactic anti-allergic agents (e.g., cromolyn sodium) and xanthines (e.g., theophylline) which appear to possess both bronchodilating and anti-inflammatory activity.

Theophylline has been a preferred drug of first choice in the treatment of asthma. Although it has been touted for its direct bronchodilatory action, theophylline's therapeutic value is now believed to also stem from anti-inflammatory activity. Its mechanism of action remains unclear. However, it is believed that several of its cellular activities are important in its activity as an anti-asthmatic, including cyclic nucleotide phosphodiesterase inhibition, adenosine receptor antagonism, stimulation of catechol-amine release, and its ability to increase the number and activity of suppressor T-lymphocytes. While all of these actually may contribute to its activity, only PDE inhibition may account for both the anti-inflammatory and bronchodilatory components. However, theophylline is known to have a narrow therapeutic index, and a wide range of untoward side effects which are considered problematic.

Of the activities mentioned above, theophylline's activity in inhibiting cyclic nucleotide phosphodiesterase has received considerable attention recently. Cyclic nucleotide phosphodiesterases (PDEs) have received considerable attention as molecular targets for anti-asthmatic agents. Cyclic 3',5'-adenosine monophosphate (cAMP) and cyclic 3',5'-guanosine monophosphate (cAMP) are known second messengers that mediate the functional responses of cells to a multitude of hormones, neurotransmitters and autocoids. At least two therapeutically important effects could result from phosphodiesterase inhibition, and the consequent rise in intracellular adenosine 3',5'-monophosphate (cAMP) or guanosine 3',5'-monophosphate (cGMP)in key cells in the pathophysiology of asthma. These are smooth muscle relaxation (resulting in bronchodilation) and anti-inflammatory activity.

It has become known that there are multiple, distinct PDE isoenzymes which differ in their cellular distribution. A variety of inhibitors possessing a marked degree of selectivity for one isoenzyme or the other have been synthesized.

The structure-activity relationships (SAR) of isozyme-selective inhibitors has been discussed in detail, e.g., in the article of Theodore J. Torphy, et al., "Novel Phosphodiesterases Inhibitors For The Therapy Of Asthma", Drug News & Prospectives, 6(4) May 1993, pages 203–214. The PDE enzymes can be grouped into five families according to their specificity toward hydrolysis of cAMP or cGMP, their sensitivity to regulation by calcium, calmodulin or cGMP, and their selective inhibition by various compounds. PDE I is stimulated by $Ca^{2+}$/calmodulin. PDE II is cGMP-stimulated, and is found in the heart and adrenals. PDE III is cGMP-inhibited, and inhibition of this enzyme creates positive inotropic activity PDE IV is cAMP specific, and its inhibition causes airway relaxation, antiinflammatory and antidepressant activity. PDE V appears to be important in regulating cGMP content in vascular smooth muscle, and therefore PDE V inhibitors may have cardiovascular activity While there are compounds derived from numerous structure activity relationship studies which provide PDE III inhibition, the number of structural classes of PDE IV inhibitors is relatively limited. Analogues of rolipram, which has the following structural formula:

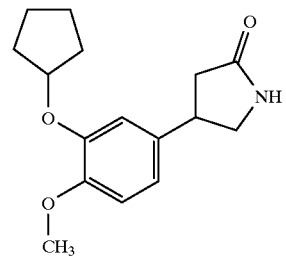

and of RO-20-1724, which has the following structural formula:

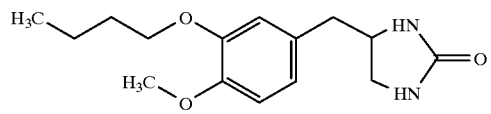

have been studied.

Rolipram, which was initially studied because of its activity as an antidepressant has been shown to selectively inhibit the PDE IV enzyme and this compound has since become a standard agent in the classification of PDE enzyme subtypes. There appears to be considerable therapeutic potential for PDE IV inhibitors. Early work focused on depression as a CNS therapeutic endpoint and on inflammation, and has subsequently been extended to include related diseases such as dementia and asthma. In-vitro, rolipram, R020-1724 and other PDE IV inhibitors have been shown to inhibit (1) mediator synthesis/release in mast cells, basophils, monocytes and eosinophils; (2) respiratory burst, chemotaxis and degranulation in neutrophils and eosinophils; and (3) mitogen-dependent growth and differentiation in lymphocytes (The PDE IV Family Of Calcium-Phosphodiesterases Enzymes, John A. Lowe, III, et al., Drugs of the Future 1992, 17(9):799–807).

PDE IV (and possibly PDE V) is present in all the major inflammatory cells in asthma including eosinophils, neutrophils, T-lymphocytes, macrophages and endothelial cells. Its inhibition causes down regulation of cellular activation and relaxes smooth muscle cells in the trachea and bronchus. On the other hand, inhibition of PDE III, which is present in myocardium, causes an increase in both the force and rate of cardiac contractility. These are undesirable side effects for an anti-inflammatory agent. Theophylline, a non-selective PDE inhibitor, inhibits both PDE III and PDE IV, resulting in both desirable anti-asthmatic effects and undesirable cardiovascular stimulation. With this well-known distinction between PDE isozymes, the opportunity for concomitant anti-inflammation and bronchodilation without many of the side effects associated with theophylline therapy is apparent. The increased incidence of morbidity and mortality due to asthma in many Western countries over the last decade has focused the clinical emphasis on the inflammatory nature of this disease and the benefit of inhaled steroids. Development of an agent that possesses both bronchodilatory and antiinflammatory properties would be most advantageous.

It appears that selective PDE IV inhibitors should be more effective with fewer side effects than theophylline. Clinical support has been shown for this hypothesis.

Attempts have therefore been made to find new compounds having more selective and improved PDE IV inhibition.

OBJECTS AND SUMMARY OF THE INVENTION

It is accordingly a primary object of the present invention to provide new compounds which are effective PDE IV inhibitors.

It is another object of the present invention to provide new compounds which act as effective PDE IV inhibitors with lower PDE III inhibition It is a further object of the present invention to provide new compounds which have a superior PDE IV inhibitory effect as compared to rolipram or other known compounds It is a further object of the present invention to provide new compounds which have a substantially equal or superior PDE IV inhibitory effect as compared to known chemical compounds, and which exhibit surprisingly greater selectivity with regard to their inhibitory effects It is another object of the present invention to provide a method of treating a patient requiring PDE IV inhibition It is another object of the present invention to provide new compounds for treating disease states associated with abnormally high physiological levels of cytokine, including tumor necrosis factor.

It is another object of the present invention to provide a method of synthesizing the new compounds of this invention It is another object of the present invention to provide a method for treating a mammal suffering from a disease state selected from the group consisting of asthma, allergies, inflammation, depression, dementia and disease states associated with abnormally high physiological levels of cytokine.

With the above and other objects in view, the present invention mainly comprises a compound of the formula:

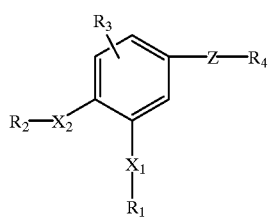

wherein:
$X_1$ and $X_2$ may be the same or different and each is O or S;
$R_1$ and $R_2$ may be the same or different and each are saturated or unsaturated straight-chain or branched alkyl groups containing from 1 to 12 carbon atoms, cycloalkyl and cycloalkyl-alkyl groups containing from 3 to 7 carbon atoms in the cycloalkyl moiety; and aryl and arylalkyl groups preferably containing from 6 to 10 carbon atoms, which are unsubstituted or substituted by lower alkyl groups having from 1 to 3 carbon atoms, one or more halogen atoms, hydroxyl groups, cyano groups, nitro groups, carboxyl groups, alkoxy groups, alkoxycarbonyl, carboxamido or substituted or unsubstituted amino groups, or heterocyclic groups containing one or more of nitrogen, oxygen and/or sulfur in the ring, or one of $R_1$ and $R_2$ are hydrogen and the other represents a hydrocarbon group as set forth above;

$R_3$ is hydrogen, halogen or a saturated or unsaturated straight-chain or branched alkyl group containing from 1 to 12 carbon atoms, a cycloalkyl and cycloalkyl-alkyl groups containing from 3 to 7 carbon atoms in the cycloalkyl moiety; or an aryl or aralkyl group preferably containing from 6 to 10 carbon atoms, which groups are unsubstituted or substituted by one or more halogen atoms, hydroxyl groups, cyano groups, nitro groups, carboxyl groups, alkoxy groups, alkoxycarbonyl, carboxamido or substituted or unsubstituted amino groups, or heterocyclic groups containing one or more of nitrogen, oxygen or sulfur in the ring;

Z is a bond or a bridging (linking) group containing from 1 to 3 carbon atoms, wherein one of the carbon atoms in the bridging group may be replaced by nitrogen, oxygen or sulfur. The carbon atoms in the bridging group may be saturated or unsaturated and may be unsubstituted or substituted with one or more substituents selected from halogen atoms (e.g., chlorine, bromine, fluorine, iodine), lower alkyl groups having from 1 to 3 carbon atoms, hydroxyl groups, cyano groups, carboxyl groups, alkoxy groups, carbonyl groups, alkoxycarbonyl groups, or substituted or unsubstituted amino groups;

$R_4$ is a 5-membered heterocyclic group which contains one or more or nitrogen, oxygen and/or sulfur atoms. The heterocyclic group may be unsubstituted or substituted with one or more halogen atoms, $C_{1-4}$ alkyl hydroxyl groups, cyano groups, nitro groups, carboxyl groups, $C_{1-4}$ alkoxylcarbonyl groups, alkoxy groups, alkoxycarbonyl, amido, carboxamido, or substituted or unsubstituted amino groups. The heterocyclic group may also be substituted with alkyl, cycloalkyl and cycloalkyl-alkyl groups containing from 3 to 7 carbon atoms in the cycloalkyl moiety, aryl or arylalkyl groups preferably containing from about 6 to about 10 carbon atoms, or heterocyclic groups containing nitrogen, oxygen or sulfur in the ring, which groups are unsubstituted or substituted by halogen atoms, hydroxyl groups, cyano groups, carboxyl groups, $C_{1-4}$ alkoxy groups, alkoxycarbonyl, carboxamido or substituted or unsubstituted amino groups, or one or more lower alkyl groups having from 1 to 3 carbon atoms; provided that $R_4$ is other than 4-imidazolinone or 4-pyrolidinone.

The term "lower alkyl" is defined for purposes of the present invention as straight or branched chain radicals having from 1 to 3 carbon atoms.

DETAILED DESCRIPTION

The compounds of the present invention, as demonstrated in the appended examples, are effective in the mediation or inhibition of PDE IV in humans and other mammals. Further, these compounds are selective PDE IV inhibitors which possess both bronchodilatory and antiinflammatory properties substantially without undesirable cardiovascular stimulation caused by PDE III inhibition. Many of these compounds have a substantially equal or superior PDE IV inhibitory effect as compared to theophylline.

The present invention is further related to a method for the treatment of allergic and inflammatory disease which comprises administering to a mammal in need thereof an effective amount of the compounds of the present invention.

The present invention is also related to a method for the mediation or inhibition of the enzymatic or catalytic activity of PDE IV activity in mammals, particularly humans, which comprises administering an effective amount of the above-described compounds of the invention to a mammal in need of PDE IV inhibition.

The compounds of the present invention may find use in the treatment of other disease states in humans and other mammals, such as in the treatment of disease states associated with a physiologically detrimental excess of tumor necrosis factor (TNF). TNF activates monocytes, macrophages and T-lymphocytes. This activation has been implicated in the progression of Human Immunodeficiency Virus (HIV) infection and other disease states related to the production of TNF and other cytokines modulated by TNF.

In certain preferred embodiments, the compounds of the present invention comprise the formula:

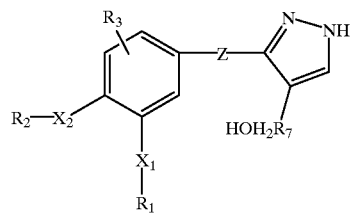

wherein:
R$_2$ is hydrogen or branched or straight chain alkyl of 1–12 carbon atoms, preferably lower alkyl, most preferably methyl or ethyl, and R$_1$ is alkyl of 1–12 carbon atoms, which may be substituted by one or more halogens, or cycloalkyl of 3–6 carbon atoms, preferably cyclopentyl which may be substituted by R$_5$ as shown in the following structural formula:

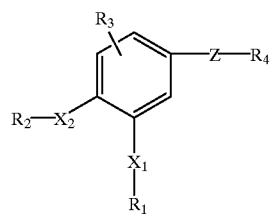

wherein
R$_5$ is hydrogen or a saturated or unsaturated straight-chain lower alkyl group containing from about 1 to about 6 carbon atoms, unsubstituted or substituted with one or more halogen atoms, hydroxyl groups, cyano groups, nitro groups, carboxyl groups, alkoxy groups, alkoxycarbonyl, carboxamido or substituted or unsubstituted amino groups;
R$_3$ is hydrogen, lower alkyl or halogen;
Z is a linkage selected from a bond, —NH—, —CH$_2$—, —CH$_2$CH$_2$—, —CH$_2$NH—, CH$_2$N(Me), NHCH$_2$—, —NH—, —CH$_2$CONH—, —NHCH$_2$CO—, —CH$_2$CO—, —COCH$_2$—, —CH$_2$COCH$_2$—, —CH(CH$_3$)—, —CH=, and —HC=CH—;
X$_1$ and X$_2$ may be the same or different and each is O or S; and
R$_4$ is an unsubstituted or substituted pyrazole, imidazole, or triazole as set forth previously.

In one preferred embodiment, R$_4$ is a substituted pyrazole having the following structure:

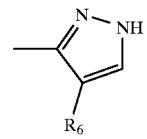

wherein R$_6$ is a substituted or unsubstituted lower alkyl having from about 1 to about 3 carbon atoms.

In a particularly preferred embodiment of the present invention, the compounds have the formula:

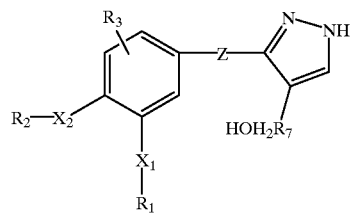

where

X$_1$ and X$_2$ may be the same or different and each is O or S;

R$_1$ is alkyl of 1–12 carbon atoms or cycloalkyl of 3–6 carbon atoms, which cycloalkyl may be substituted by one or more alkyl groups or by one or more halogens;

R$_2$ is hydrogen or alkyl of 1–12 carbon atoms;

R$_3$ is hydrogen, lower alkyl or halogen;

Z is a linkage selected from a bond, —NH—, —CH$_2$—, —CH$_2$CH$_2$—, —CH$_2$NH—, NHCH$_2$—, —NH—, —CH$_2$N(Me)—,—CH$_2$CONH—, —NHCH$_2$CO—, —CH$_2$CO—, —COCH$_2$—, —CH$_2$COCH$_2$—, —CH(CH$_3$)—, —CH=, and —HC=CH—; and R$_7$ is C or CH$_2$C.

One preferred compound of the present invention is 3-(3-cyclopentyloxy-4-methoxybenzylamino)-4-hydroxymethyl pyrazole.

In certain preferred embodiments, compounds of the present invention are prepared by the two-step process shown below for the preferred compound of the invention, 3-(3-cyclopentyloxy-4-methoxybenzylamino)-4-hydroxymethyl pyrazole.

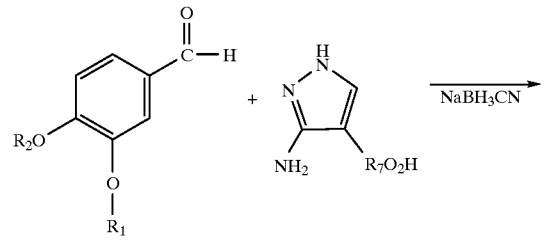

-continued

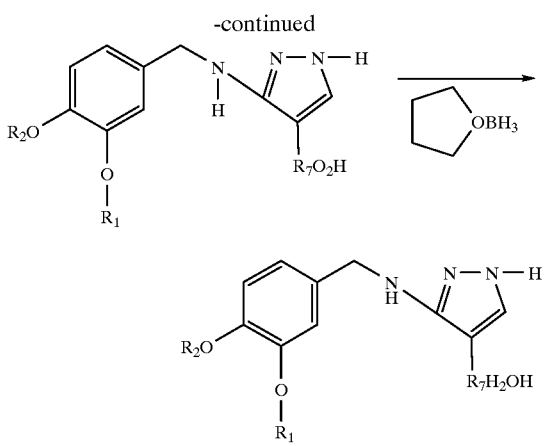

The condensation of 3-cyclopentyloxy-4-methoxybenzaldehyde with 3-amino-4-pyrazolecarboxylic acid in the presence of sodium cyanoborohydride produces 3-(3-cyclopentyloxy-4-methoxybenzyl-amino)-4-pyrazolecarboxylic acid in 48% yield. Treatment with excess borane-tetrahydrofuran complex in tetrahydrofuran solution gives 3-(3-cyclopentyloxy-4-methoxybenzylamino)-4-hydroxymethylpyrazole (Example 1) in 40% yield.

In other embodiments where $R_4$ is an imidazole, triazole or pyrazole, the compounds can be synthesized by reductively condensing 3-cyclopentyloxy-4-methoxybenzaldehyde with amino heterocycles using sodium cyanoborohydride. The reaction is shown below.

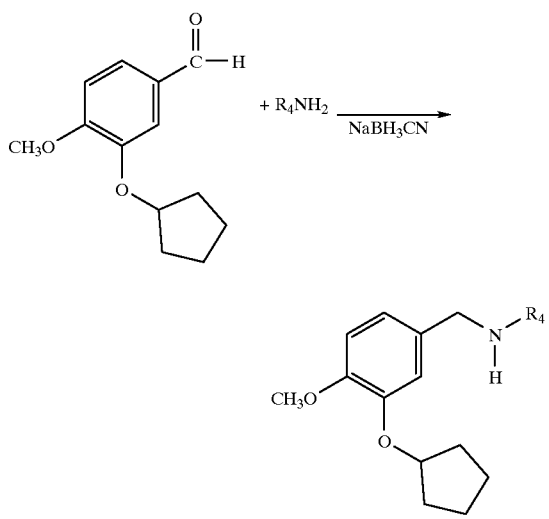

The compounds of the present invention have been found to be highly effective PDE IV inhibitors, the inhibition of which is in fact significantly and surprisingly greater than that of theophylline.

Thus, the concentration which yields 50% inhibition of PDE IV ($IC_{50}$) for 3-(3-cyclopentyloxy-4-methoxybenzylamino)-4-hydroxymethyl pyrazole is 16 nM (0.016 $\mu$M), whereas the $IC_{50}$ for rolipram when run in the same assay was 4.5 $\mu$M. Historically, the $IC_{50}$ for rolipram is considered to be 3.5 $\mu$M. In any case, it is apparent that Example 1 of the present invention is several hundred times as effective as a PDE IV inhibitor as compared to rolipram.

By comparison, PDE III inhibition of Example 1 of the present invention is within 1 order of magnitude of that of rolipram, and therefore relative to the percentage increase in PDE IV inhibition, it is clear that the compound of the invention is much more highly selective as a PDE IV inhibitor than rolipram.

Accordingly, the compounds of the present invention can be administered to anyone requiring PDE IV inhibition. Administration may be orally, topically, by suppository, inhalation or insufflation, or parenterally.

The present invention also encompasses all pharmaceutically acceptable salts of the foregoing compounds. One skilled in the art will recognize that acid addition salts of the presently claimed compounds may be prepared by reaction of the compounds with the appropriate acid via a variety of known methods. Alternatively, alkali and alkaline earth metal salts are prepared by reaction of the compounds of the invention with the appropriate base via a variety of known methods. For example, the sodium salt of the compounds of the invention can be prepared via reacting the compound with sodium hydride.

Various oral dosage forms can be used, including such solid forms as tablets, gelcaps, capsules, caplets, granules, lozenges and bulk powders and liquid forms such as emulsions, solution and suspensions. The compounds of the present invention can be administered alone or can be combined with various pharmaceutically acceptable carriers and excipients known to those skilled in the art, including but not limited to diluents, suspending agents, solubilizers, binders, disintegrants, preservatives, coloring agents, lubricants and the like.

When the compounds of the present invention are incorporated into oral tablets, such tablets can be compressed, tablet triturates, enteric-coated, sugar-coated, film-coated, multiply compressed or multiply layered. Liquid oral dosage forms include aqueous and nonaqueous solutions, emulsions, suspensions, and solutions and/or suspensions reconstituted from non-effervescent granules, containing suitable solvents, preservatives, emulsifying agents, suspending agents, diluents, sweeteners, coloring agents, and flavorings agents. When the compounds of the present invention are to be injected parenterally, they may be, e.g., in the form of an isotonic sterile solution. Alternatively, when the compounds of the present invention are to be inhaled, they may be formulated into a dry aerosol or may be formulated into an aqueous or partially aqueous solution.

In addition, when the compounds of the present invention are incorporated into oral dosage forms, it is contemplated that such dosage forms may provide an immediate release of the compound in the gastrointestinal tract, or alternatively may provide a controlled and/or sustained release through the gastrointestinal tract. A wide variety of controlled and/or sustained release formulations are well known to those skilled in the art, and are contemplated for use in connection with the formulations of the present invention. The controlled and/or sustained release may be provided by, e.g., a coating on the oral dosage form or by incorporating the compound(s) of the invention into a controlled and/or sustained release matrix.

Specific examples of pharmaceutically acceptable carriers and excipients that may be used for formulate oral dosage forms, are described in the Handbook of Pharmaceutical Excipients, American Pharmaceutical Association (1986), incorporated by reference herein. Techniques and compositions for making solid oral dosage forms are described in Pharmaceutical Dosage Forms: Tablets (Lieberman, Lachman and Schwartz, editors) 2nd edition, published by Marcel Dekker, Inc., incorporated by reference herein. Techniques and compositions for making tablets (compressed and molded), capsules (hard and soft gelatin) and pills are also described in *Remington's Pharmaceutical Sciences* (Arthur Osol, editor), 1553–1593. (1980), incorporated herein by reference Techniques and composition for making liquid oral dosage forms are described in *Pharmaceutical Dosage Forms: Disperse Systems,* (Lieberman, Rieger and Banker, editors) published by Marcel Dekker, Inc., incorporated herein by reference.

When the compounds of the present invention are incorporated for parenteral administration by injection (e.g., continuous infusion or bolus injection), the formulation for parenteral administration may be in the form of suspensions, solutions, emulsions in oily or aqueous vehicles, and such formulations may further comprise pharmaceutically necessary additives such as stabilizing agents, suspending agents, dispersing agents, and the like. The compounds of the invention may also be in the form of a powder for reconstitution as an injectable formulation.

The dose of the compounds of the present invention is dependent upon the affliction to be treated, the severity of the symptoms, the route of administration, the frequency of the dosage interval, the presence of any deleterious side-effects, and the particular compound utilized, among other things.

The PDE IV inhibitory compounds of the present invention may be examined for their PDE IV inhibitory effects via the techniques set forth in the following examples, wherein the ability of the compounds to inhibit PDE IV isolated from bovine tracheal smooth muscle is set forth.

DESCRIPTION OF THE PREFERRED EMBODIMENTS

The following examples illustrate various aspects of the present invention, and are not to be construed to limit the claims in any manner whatsoever.

EXAMPLE 1

3-(3-cyclopentyloxy-4-methoxybenzylamino)-4-hydroxymethylpyrazole

The above-mentioned compound was prepared by a two-step process as set forth below:

A: 3-(3-cyclopentyloxy-4-methoxy-benzylamino)-4-pyrazolecarboxylic acid

A suspension of 3-amino-4-pyrazole carboxylic acid (3.56 g, 28 mmol) in 400 ml of methanol and 3-cyclopentyloxy-4-methoxybenzaldehyde (5.06 g, 23 mmol) was stirred at room temperature for 16 hours with sodium cyanoborohydride, 1.85 g (95% pure, 28 mmol). The methanol was evaporated under reduced pressure and the residue was taken up in 100 ml of 15% sodium hydroxide and extracted twice with 100 ml portions of ether. The aqueous layer was acidified to pH 5 with 5N hydrochloric acid and extracted twice with 100 ml portions of ethyl acetate. The ethyl acetate was dried over sodium sulfate and evaporated. The residue was triturated with ether to give 3.7 g of 3-(3-cyclopentyloxy-4-methoxybenzylamino)-4-pyrazolecarboxylic acid (48.7%). Pure 3-(3-cyclopentyloxy-4-methoxybenzylamino)pyrazole carboxylic acid shows mp. 134–136° C. after crystallization from methanol.

B: 3-(3-cyclopentyloxy-4-methoxybenzylamino)-4-hydroxymethylpyrazole

Pure 3-(3-cyclopentyloxy-4-methoxybenzylamino)-4-pyrazolecarboxylic acid (compound 3) (1.32 g, 4.0 mmol) was dissolved in 50 ml of THF and cooled to −15° C. under nitrogen. Borane-tetrahydrofuran (30 ml of 1M solution, 30 mmol) was added over 30 minutes and the resulting solution was stirred for 72 hours at room temperature. Methanol (30 ml) was added to the reaction and the solvent was evaporated under reduced pressure. The residue was treated with 160 ml of methanol and evaporated again. The crude product was treated with 30 ml of 10% aqueous ammonia and some brine and then extracted with three 50 ml portions of ethyl acetate. Evaporation of the solvent afforded 1.1 g of crude 3-(3-cyclopentyloxy-4-methoxybenzylamino)-4-hydroxymethylpyrazole which was purified by flash chromatography on 30 g of flash chromatography silica gel. Elution with ethyl acetate/hexane (1:4) afforded a small amount of material which was discarded. Elution with 60 ml of 1:1 ethyl acetate/hexane gave 600 mg of 3-(3-cyclopentyloxy-4-methoxybenzylamino)-4-hydroxymethylpyrazole which was recrystallized from 2 ml of toluene to give 500 mg of pure 3-(3-cyclopentyloxy-4-methoxybenzylamino)-4-hydroxymethylpyrazole (compound 4) mp 129–130° C.

EXAMPLE 2

3-(3-Cyclopentyloxy-4-methoxybenzyl-amino)-4-pyrazolecarboxamide

To a stirred suspension of 3-amino-4-pyrazolecarboxamide hemisulfate (0.005 mole) was added 0.14 g of potassium hydroxide (KOH), 3-cyclopentyloxy-4-methoxybenzaldehyde (0.88 g, 0.004 mole), and 95% sodium cyanoborohydride (0.33 g, 0.004 mol). Stirring was continued at room temperature for 24 hours after which KOH (0.56 g) was added and the solvent was evaporated under reduced pressure. The residue was treated with 50 ml of brine and extracted twice with 50 ml portions of ethyl acetate. The ethyl acetate was evaporated under reduced pressure and the residue was triturated with ether to give 0.4g of the crude title compound Crystallization from 15 ml of acetone gave 0.25 g (15%) of the pure title compound, mp 128–130° C.

EXAMPLE 3

3-(3-Cyclopentyloxy-4-methoxybenzylamino)-1,2,4-triazole

To a stirred solution of 3-amino-1,2,4-triazole (1.5 g, 0.018 mol), 7.5 ml of 1N HCl, and 50 ml of methanol was added 3-cyclopentyloxy-4-methoxybenzaldehyde (3.3 g, 0.015 mol) and sodium cyanoborohydride (0.945 g, 0.015 mol). A precipitate formed slowly and after 20 hours the precipitate was filtered and recrystallized from methanol (135 ml) to give 1.0 g (0.0034 mol. 23%) of the title compound, mp 203–204° C.

EXAMPLE 4

3-(3-Cyclopentyloxy-4-methoxybenzylamino) pyrazole

To a solution of 3-aminopyrazole (1.5 g, 0.018 mol) in 50 ml of methanol and 7.5 ml of 1N aqueous HCl was added 3-cyclopentyloxy-4-methoxybenzaldehyde (3.3 g, 0.015 mol) and 95% sodium cyanoborohydride (1.0 g, 0.015 mol). The solution was stirred at room temperature for 20 hours after which concentrated aqueous hydrochloric acid (Hcl) was added to pH 2. The solvent was evaporated at reduced pressure and the residue was extracted twice with 50 ml portions of ether. The ether extracts were discarded and the aqueous solution was brought to pH 10 with 5N aqueous NaOH. The mixture was extracted twice with 50 ml portions of ethyl acetate. The combined ethyl acetate extracts were dried (MgSO$_4$) and evaporated. The solid residue was triturated with ether to give the pure title compound (1.3 g, 30%), mp 106–110° C.

EXAMPLE 5

5-(3-Cyclopentyloxy-4-methoxybenzylamino)-1,2,3-triazole

To a stirred solution of 5-amino-1,2,3-triazole (3.0 g, 0.036 mol) in 100 ml of methanol and 15 ml of 1N HCl was added sodium cyanoborohydride (1.89 g, 0.030 mol) and 3-cyclopentyloxy-4-methoxybenzaldehyde (6.6 g, 0.30 mol). The reaction mixture was stirred at room temperature for 64 hours and then acidified to pH 2 with concentrated HCl. The solution was evaporated at reduced pressure and the residue was treated with water (100 ml) and extracted twice with 100 ml portions of ethyl acetate. The ethyl acetate extracts were combined and extracted twice with 50 ml portions of 3N HCl and then discarded. The aqueous extracts were combined with the original aqueous layer and basified to pH 12 with potassium hydroxide pellets. The alkaline solution was extracted twice with 100 ml portions of ethyl acetate. The ethyl acetate extracts were combined and evaporated to give a solid which was crystallized from ethyl acetate to give 2.9 g (34%) of the title compound mp 113–114° C. collected in two crops.

EXAMPLE 6

2-(3-Cyclopentyloxy-4-methoxybenzylamino) imidazole

A stirred suspension of 2-aminoimidazole sulfate (5.67 g, 0.043 mol) in 100 ml of methanol was treated with solid KOH (0.65 g, 0.011 mol) followed by 3-cyclopentyloxy-4-methoxybenzaldehyde (7.26 g, 0.033 mol). To this mixture was added dropwise over 30 minutes solution of 95% sodium cyanoborohydride (2.2 g, 0.33 mol) in methanol (30 ml). The reaction mixture was stirred at room temperature for 64 hours after which solid KOH (2.45 g, 0.055 mol) was added. After the KOH had dissolved, the mixture was filtered and the filtrate was evaporated under reduced pressure. The residue was treated with saturated NaCl and extracted three times with 50 ml portions of ethyl acetate. The combined ethyl acetate extracts were extracted twice with 5N aqueous HC1. Evaporation of the ethyl acetate yielded 5.5 g of unreacted 3-cyclopentyloxy-4-methoxybenzaldehyde. The aqueous HCl extract was basified to pH 12 with solid KOH and extracted twice with 50 ml portions of ethyl acetate. Evaporation of the ethyl acetate afforded 2.4 g of a brown oil which was purified by flash chromatography over 40 g of flash chromatography silica gel. Elution with methylene chloride- methanol mixtures afforded 1.8 g of the title compound eluted with 5% methanol-methylene chloride. The 1.8 g of material was treated with solution of picric acid (5 g, 0.021 mol) in 50 ml of ethanol. The picrate (1.9 g) was collected and recrystallized from 25 ml of ethanol to give 1.7 g of the pure picrate. The picrate (1.5 g) was dissolved in 200 ml of ethyl acetate and extracted 5 times with 25 ml portions of 2N aqueous LiOH. The ethyl acetate solution was evaporated and the residue (0.9 g) was purified by flash chromatography over 40 g of silica gel, eluting with methanol- methylene chloride mixtures to give 0.5 g of the material which was crystallized from 15 ml of ethyl acetate to give 0.3 g (3%) of the pure title compound, mp 114–115° C.

EXAMPLE 7

3-(3-Cyclopentyloxy-4-methoxybenzyl-amino)-4-pyrazolecarboxylic acid

To a suspension of 3-aminopyrazole-4-carboxylic acid (3.56 g, 0.023 mol) in 400 ml of methanol was added 3-cyclopentyloxy-4-methoxybenzaldehyde (5.06 g, 0.023 mole) and 95% sodium cyanoborohydride (1.85 g, 0.028 mol). The reaction mixture was stirred for 16 hours and then the methanol was evaporated under reduced pressure. The residue was treated with 100 ml of 15% aqueous NaOH and extracted twice with 100 ml portions of ether. The aqueous layer was acidified to pH 5 with 5N aqueous HCl and extracted twice with 100 ml portions of ethyl acetate. The ethyl acetate extracts were evaporated under reduced pressure and the residue was triturated with ether to give 3.7 g (49%) of the title compound, mp 134–136°, after recrystallization from methanol.

EXAMPLE 8

5-(3-Cyclopentyloxy-4-methoxybenzal hydantoin

To a stirred solution of diethyl 5-hydantoylphosphonate (10 g, 42.3 mmol) and triethylamine (5.70 g, 56 mmol), in dry acetonitrile (100 ml) at room temperature was added a solution of 3-cyclopentyloxy-4-methoxybenzaldehyde (8 g, 36.3 mmol) in dry acetonitrile (75 ml), dropwise over 30 minutes. The resulting mixture was stirred at room temperature overnight, after which volatiles were removed in vacuo. The residue was diluted with 0.05N HCl (120 ml) and the precipitate collected by filtration. Recrystallization of this material with methylene chloride/methanol/diethyl ether afforded the title compound as a pale yellow solid (8.54 g). m.p. 220–222° C.

$^1$H NMR (CDCl$_3$; 250 MHz) δ7.72 (brs, 1H), 7.66 (brs, 1H), 6.90 (m, 3H), 6.66 (s, 1H), 4.79 (m, 1H), 3.88 (s, 3H), 1.84 (m, 6H), 1.62 (m, 2H).

EXAMPLE 9

4-(3-Cyclopentyloxy-4-methoxybenzyl)-5-methyl-pyrazol-3-one

A. (E)/(Z) Ethyl 2-acetyl-3-(3-cyclopentyloxy-4-methoxyphenyl)-2-propenoate

To a stirred solution of 3-cyclopentyloxy-4-methoxybenzaldehyde (4.0 g, 22.69 mmol) and ethyl acetoacetate (2.95 g, 22.67 mmol) in benzene (60 ml) were added piperidine (104 mg, 1.22 mmol) and glacial acetic acid (286 mg, 4.76 mmol) in one portion. The resulting solution was refluxed at 85° C. for 3 hours with continuous removal of water. Further piperidine (208 mg, 2.44 mmol) and glacial acetic acid (858 mg, 14.28 mmol) were added and refluxing continued for a further 5 hours. The mixture was cooled to room temperature and diluted with diethyl ether (300 ml). The organics were washed successively with 5% aqueous HCl (100 ml) and water (2 ×100 ml) The resulting etheral extracts were dried (Na$_2$SO$_4$) and concentrated in vacuo to give a deep orange oil. The oil was purified by flash chromatography (Sio$_2$; ethyl acetate/hexane (3:7)) to afford the title compound as an orange oil (983 mg).

$^1$H (CDCl$_3$; 250 MHz) δ7.57 and 7.46 (2s, 1H), 6.92 (m, 3H), 6.92 (m, 3H), 4.70 (m, 1H), 4.34 and 4.26 (2q, 2H), 3.87 and 3.86 (2s, 3H), 2.39 and 2.37 (2s, 3H), 1.87 (m, 6H), 1.62 (m, 2H), 1.31 (t, 3H).

B. Ethyl 2 acetyl-3-(3-cyclopentyl-oxy-4-methoxyhenyl)-propanoate

A solution of (E)/(Z) ethyl 2-acetyl-3-(3-cyclopentyloxy-4-methoxyphenyl)-2-propenoate (745 mg, 2.24 mmol) in ethyl acetate (20 ml) containing palladium on activated carbon (10% palladium, 25 mg) was hydrogenated at 40 p.s.i. for 5 hours at room temperature. The mixture was filtered through celite and the filter cake washed with ethyl acetate (2×25 ml). The filtrate was concentrated in vacuo and purified by flash chromatography (SiO$_2$; ethyl acetate/hexane (3:7)) to afford the title compounds as a pale yellow oil (585 mg). R$_f$ (SiO$_2$; ethyl acetate/hexane (3:7)) 0.45.

C. 4-(3-Cyclopentyloxy-4-methoxy-benzyl)-5-methyl-pyrazol-3-one

To a stirred solution of ethyl 2-acetyl-3-(3-cyclopentyloxy-4-methoxyphenyl)-propanoate (585 mg, 1.74 mmol) in absolute ethanol (10 ml) at 0° C. was added hydrazine monohydrate (87 mg, 1.74 mmol) in one portion. The resulting solution was stirred at 0° C. for 45 minutes and then refluxed at 80° C. for 3 hours. After cooling to room temperature, the reaction mixture was concentrated in vacuo and purified by flash chromatography (SiO$_2$; methylene chloride/ethanol/ammonia (4:1:0.1)) to afford the title compound as a white solid (343 mg). m.p. 186–187° C.

$^1$H NMR (CD$_3$OD; 250 MHz) δ6.78 (m, 3H), 4,73 (m, 1H) , 3.76 (s, 3H), 3.56 (s, 2H), 2,03 (s, 3H), 1.80 (m, 6H), 1.59 (m, 2H).

EXAMPLE 10

4-[1-(3-Cyclopentyloxy-4-methoxy-phenyl)ethyl]-5-methylpyrazol-3-one

A. N-Methoxy-N-methyl-3-(3-cyclopentyloxy-4-methoxyphenyl)-prop-2-enamide

To a stirred solution of diethyl (N-methoxy-N-methyl-carbamoylmethyl) phosphonate (2.60 g, 10.90 mmol) in dry tetrahydrofuran (50 ml) at –78° C. was added lithium diisopropylamide (1.5M solution in cyclohexane, 7.33 ml, 11 mmol) dropwise over 3 minutes. The resulting solution was stirred at –78° C. for 30 minutes, after which time 3-cyclopentyloxy-4-methoxybenzaldehyde (1.5 g, 6.81 mmol) in dry tetrahydrofuran (5 ml) portion. The reaction was allowed to warm to room temperature and stirring continued overnight. After which time the reaction mixture was diluted with water (25 ml) and the tetrahydrofuran removed in vacuo. The aqueous residue was diluted with brine (25 ml) and extracted with methylene chloride (3×60 ml) The organic extracts were dried (Na$_2$SO$_4$) and evaporated in vacuo to give a yellow liquid. The liquid was purified by flash chromatography (SiO$_2$; hexane/ethyl acetate (65:35)) to afford the title compound as a pale yellow liquid (1.986 g). R$_f$(SiO$_2$; ethyl acetate/hexane (35:65)) 0.15

B. (E)-4-(3-Cyclopentyloxy-4-methoxyphenyl)-3-buten-2-one

To a stirred solution of N-methoxy-N-methyl-3-(3-cyclopentyloxy-4-methoxyphenyl)prop-2-enamide (1.986 g, 6.50 mmol) in dry tetrahydrofuran (15 ml) at –78° C. was added methyl lithium (1.4M solution in hexanes, 10.20 ml, 14.3 mmol) dropwise over 3 minutes. The resulting solution was stirred for 1 hour at 0° C., after which time the reaction mixture was diluted with 5% HCl in methanol (20 ml) at 0° C., and partitioned between brine (35 ml) and an equal volume of methylene chloride and diethyl ether (100 ml). The organics were dried (Na$_2$SO$_4$) and concentrated in vacuo to give a light yellow oil. The oil was purified by flash chromatography (SiO$_2$; ethyl acetate/hexane (35:65)) to afford the title compound as a colorless oil (1.642 g).

$^1$H NMR (CDCl$_3$; 250 MHz) δ7.43 (d, J=16.2Hz, 1H) , 7.08 (m, 2H) , 6.85 (d, 1H), 6.57 (d, J=16.2Hz, 1H), 4.78 (m, 1H), 3.87 (s, 3H), 2.36 (s, 3H), 1.89 (m, 6H), 1.62 (m, 2H).

C. [[4-(3-Cyclopentyloxy-4-methoxyphenyl)-2-penten-2-yl]oxy]tributylsilane

To a stirred suspension of cuprous iodide (1.15 g, 6.045 mmol) in dry tetrahydrofuran (10 ml) at 0° C. was added methyl lithium (1.4M solution in hexanes, 8.635 ml, 12.09 mmol) dropwise over 3 minutes. The resulting solution was stirred at 0° C. for 30 minutes, then cooled to –78° C. and chlorotributylsilane (3.54 g, 15.07 mmol) in dry tetrahydrofuran (5 ml) added so that the temperature of the reaction mixture did not rise above –60° C. After addition was complete the reaction was stirred at –78° C. for 10 minutes then (E)-4-(3-cyclopentyloxy-4-methoxyphenyl)-3-buten-2-one (787 mg, 3.02 mmol) in dry tetrahydrofuran (5 ml) added dropwise over 3 minutes. The resulting solution was stirred at –78° C. for 45 minutes and quenched at –78° C. by the addition of aqueous saturated NaHCO$_3$ (25 ml) and water (20 ml).

After warming to room temperature, the precipitate was removed by filtration and the filtrate extracted with pentane (3×70 ml). The organics were washed with water (20 ml), brine (20 ml) and dried (Na$_2$SO4) and concentrated in vacuo to give an oil. The oil was purified by flash chromatography (SiO2;1) hexane 2) hexane/ethyl acetate (9:1)) to afford the title compound (contaminated with tributylsilane/chlorotributylsilane) as a colorless oil (3.33 g). R$_f$ (SiO$_2$; hexane/ethyl acetate (9:1)) 0.42

D. Methyl 2-acetyl-3-(3-cyclopentyloxy-4-methoxyphenyl)-butanoate

To a stirred solution of [[4-(3-(cyclopentyloxy-4-methoxyphenyl)-2-penten-2-yl]oxy]tributylsilane prepared as detailed above, (3.38 g, containing approximately 3.0 mmol of the desired compound and 8.0 mmol of chlorotributylsilane/tributylsilane) in dry tetrahydrofuran (10 ml) at 0° C. was added methyl lithium (1.4M in diethyl ether, 9.37 ml, 13.12 mmol) dropwise over 3 minutes. The resulting clear solution was stirred for 18 hours at room temperature, then cooled to –78° C. Hexamethylphosphoramide (537 g, 3.0 mmol) and methylcyanoformate (280 mg, 3.3 mmol) in dry etrahydrofuran (3 ml) were added and the mixture stirred at –78° C. for 30 minutes. After warming to 0° C. the reaction mixture was portioned between water (40 ml) and diethyl ether (100 ml). The organics were washed with bring (30 ml), dried (Na$_2$SO$_4$) and evaporated in vacuo to give an oil. The oil was purified by flash chromatography (SiO$_2$:hexane/ethyl acetate (85:15)) to afford the title compound as a colorless oil (362 mg). R$_f$ (SiO$_2$; ethyl acetate-.hexane (1:4) 0.26 and 0.22 mixture of isomers.

E. 4-[1-(3-Cyclopentyloxy-4-methoxyphenyl) ethyl]-5-methyl-pyrazol-3-one

To a stirred solution of methyl 2-acetyl-3-(3-cyclopentyloxy-4-methoxyphenyl)-butanoate (362 mg, 1.08 mmol) in absolute ethanol (10 ml) at 0° C. was added hydrazine monohydrate (54 mg, 1.08 mmol) in one portion. The resulting solution was stirred at 0° C. for 45 minutes and then refluxed at 80° C. for 3 hours. Further hydrazine monohydrate (15.6 mg, 3.1×10$^{-4}$ mol) was added and refluxing continued for a further 3 hours. After cooling to room temperature, the reaction mixture was concentrated in vacuo and purified by flash chromatography (SiO$_2$; methylene chloride/ethanol/ammonia (97.5:2.5:0.25)) to afford the title compound as a white solid (76 mg).

$^1$H (CDCl$_3$; 250 MHz) δ6.80 (m, 3H), 4.72 (m, 1H), 3.93 (q, 1H), 3.79 (s, 3H), 2.00 (s, 3H), 183 (m, 6H), 1.60 (d, 3H), 1.57 (m, 2H).

EXAMPLE 11

5-(3-Cyclopentyloxy-4-methoxybenzal)hydantoin

A solution of 3-(3-cyclopentyloxy-4-methoxybenzal)hydantoin (1 g, 3.30 mmol) in ethanol/methylene chloride ((3:1) 50 ml) containing palladium on activated carbon (5% Pd, 200 mg) was hydrogenated at 40 p.s.i. for 6 hours at room temperature. The mixture was filtered through celite and the filter cake washed with methylene chloride (2×40 ml). The filtrate was concentrated in vacuo and purified by flash chromatography (SiO$_2$; Tnethylene chloride/ethanol/ammonia (96:4:0.4)) to afford the title compound as a white solid (578 mg). m.p. 151–153° C.

$^1$H NMR (CDCl$_3$; 250 MHz) δ8.41 (brs, 1H), 6.74 (m, 3H), 5.79 (brs, 1H), 4.73 (brs, 1H), 4.24 (dd, 1H), 3.80 (s, 3H), 2.98 (AB system 2×dd, 2H), 1.83 (m, 6H), 1.59 (m, 2H).

EXAMPLE 12

Ethyl 3-(3-cyclopentyloxy-4-methyoxybenzylamino)pyrazole-4-carboxylate

A. solution of ethyl 3-aminopyrazole 4-carboxylate (70 g, 0.45 mol) and 3-cyclopentyloxy-4-methoxybenzaldehyde (100 g, 0.45 mol) in methanol (400 mL) was treated with sodium cyanoborohydride (19.0 g, 0.30 mol) and sodium acetate (2.0 g, 0.024 mol) in a stirred reaction vessel equipped with pH stat attached to a syringe pump and a syringe filled with 3N acetic acid in methanol. The pH stat was set to maintain pH 7. The acetic acid solutias the react as the reaction proceeded. After 24 hours, 169 mL of acetic acid solution had been added and no aldehyde remained in the reaction mixture by TLC (silica gel, 10% methanol/methylene chloride) and 3-cyclopentyloxy-4-methoxybenzaldehyde (19.0 g, 0.086 mol) was added to the reaction mixture. After 30 hours, a total of 216 mL of acetic acid solution had been added and 3-cyclopentyloxy-4-methoxybenzaldehyde (16 g, 0.072 mol) was added to the reaction mixture. After 48 hours, 263 mL of acetic acid solution had been added and additional 3-cyclopentyloxy-3-methoxybenzaldehyde (29 g, 0.13 mol) was added to the reaction mixture. After 76 hours, 320 mL of acetic acid solution had been consumed and the reaction mixture was evaporated under reduced pressure. The residue was partitioned between water (400 mL) and ethyl acetate (400 mL) and the ethyl acetate was evaporated under reduced pressure to give 240 g of crude product. The crude product was purified by flash chromatography over 900 g of flash chromatography silica gel and eluted with methanol-methylene chloride mixtures. Elution with pure methylene chloride afforded by-product 3-cyclopentyloxy-4-methoxybenzyl alcohol. Elution with 1–25% methanol-methylene chloride gave 91 g (42%) of nearly pure ethyl 3-(3-cyclopentyloxy-4-methoxybenzyl-amino)pyrazole-4-carboxylate. A portion of this ethyl 3-(3-cyclopentyloxy-4-methoxybenzylamino)pyrazole carboxylate (29 g) was recrystallized from methyl t-butyl ether to give 16.8 g of pure ethyl 3-(3-cyclopentyloxy-4-methoxybenzyl-amino)pyrazole-4-carboxylate, mp 102–104°.

EXAMPLE 13

3-(3-cyclopentyloxy-4-methoxybenzylamino)-4-cyanopyrazole

A solution of 3-amino-4-cyanopyrazole (5.0 g, 0.16 mol), 3-cyclopentyloxy-4-methoxybenzaldehyde (10.0 g, 0.045 mol) and sodium acetate (0.2 g, 2.4 mol) in methanol (70 mL) was placed in a stirred reaction flask equipped with a pH stat controlling a syringe pump and syringe filled with 3N acetic acid in methanol. The pH stat was set to maintain pH 7. After 24 hours, more 3-cyclopentyloxy-4-methoxybenzaldehyde (7.0 g, 0.031 mol) was added and the reaction was continued. After 48 hours, more 3-cyclopentyloxy-4-methoxybenzaldehyde (4.0 g, 9.0 mmol) and soduim cyanoborohydride (0.5 g, 7.9 mmol) was added and the reaction was continued. After 72 hours, more sodium cyanoborohydride (0.5 g, 7.9 mmol) was added and after 96 hours, the reaction was stopped and the solvent was removed under reduced pressure. The residue was partitioned between ethyl acetate (75 mL) and water (50 mL). The ethyl acetate layer was washed with water (2×50 mL) and evaporated. The crude product was chromaotgraphed over 200 g of flash chromatography silica gel. Elution with 2% methanol/methylene chloride removed some impurities including 3-cyclopentyloxy-4-methoxybenzyl alcohol. Continued elution with methanol/methylene chloride mixtures of increasing methanol concentration afforded 8 g (56%) of nearly pure title compound. Pure 3-(3-cyclopentyloxy-4-methoxy-benzylamino)-4-cyanopyrazole, mp 159–160° was obtained by recrystallization from methanol.

EXAMPLE 14

3-(3-cyclopentyloxy-4-methoxybenzylamino)-4-methylpyrazole

A stirred solution of ethyl 3-(3-cyclopentyloxy-4-methoxybenzylamino-pyrazole-4-carboxylate) (from EXAMPLE 12) (5.4 g, 0.015 mol) in THF (50 mL) at 0° was treated with sodium bis (2-methoxyethoxy)aluminum hydride (0.03 mole), 9 mL of 3.4M solution in toluene. After 3 hours, another 9 mL portion of the sodium bis (2-methoxyethoxy)aluminum hydride solution (0.03 mol) was added. The reaction was stirred overnight at room temperature and methanol (20 mL) was added. The reaction mixture was diluted with water and extracted with ethyl acetate. The ethyl acetate extracts were washed with water and evaporated under reduced pressure. The residue crystallized upon trituration with hexanes. Pure title compound (1.7 g, 38%), mp 76–77°, was obtained after two crystallizations from methyl t-butylether.

EXAMPLE 15

3-(3-cyclopentyloxy-4-methoxybenzylamino)-4-methoxymethylpyrazole

A solution of 3-(3-cyclopentyloxy-4-methoxybenzylamino)-4-hydroxymethylpyrazole (1.0 g, 3.15 mmol) and p-toluenesulfonic acid monohydrate (0.2 g, 1.0 mmol) in methanol (100 mL) was kept at room temperature for 10 min. The reaction mixture was neutralized with 1N aqueous sodium hydroxide and evaporated under reduced pressure at room temperature. The residue was partitioned between water (50 mL) and ethyl acetate (50 mL). The layers were separated and the aqueous layer was extracted with ethyl acetate (10 mL) The combined ethyl acetate layers were washed with water and evaporated under reduced pressure. The residue was taken up in a small volume of methylene chloride and applied to a 4 mm silica gel disk on a Chromatotron. Elution with 525 mL of methylene chloride and 275 mL of 1% methanol/methylene chloride removed some impure material. Continued elution with 75 mL of 1% methanol/methylene chloride afforded 380 mg (36%) of pure 3-(3-cyclopentyloxy-4-methoxybenzylamino)-4-methyoxymethylpurazole, mp. 112–115°.

EXAMPLE 16 ethyl 3-(3-cyclopentyloxy-4-methoxyphenyl-1-ethen-2-yl)pyrazole-4-carboxylate

A four-step process as set forth below was used to prepare the title compound.

A: Ethyl 5-(3-cyclopentyloxV-4-methoxyphenyl)-3-oxo-5-hydroxypentanoate

Sodium hydride (6.0 g of 60% sodium hydride in mineral oil, 0.15 mol) was placed in a 3-neck flask equiped with a mechanical stirrer under nitrogen and washed twice with hexanes. THF (200 mL) was added and the mixture was cooled in an ice bath. Ethyl acetoacetate (17.6 g, 0.135 mol) was added dropwise and the mixture was stirred for 10 minutes after the addition. Butyllithium (0.35 mol, 84 mL of 1.6M solution in hexanes) was added dropwise to give an orange solution. A solution of 3-cyclopentyloxy-4-methoxybenzaldehyde (29.6 g, 0.135 mol) in THF (100 mL) was added dropwise. After 10 minutes, the cold solution was treated with concentrated hydrochloric acid (26 mL, 0.29 mol), water (65 mL) and ether (500 mL). The ether layer was separated and washed with saturated brine (3×300 mL). The ether was evaporated to give 46.5 g of crude title compound. The crude product was dissolved in a small amount of 30% methylene chloride/hexanes and purified by chromatography over 400 g of flash chromatography silica gel. Elution with methylene chloride/hexane mixtures removed 9 g of starting aldehyde. Elution with 1% methanol/methylene chloride afforded the ethyl 5-(3-cyclopentyloxy-4-methoxyphenyl)-3-oxo-5-hydroxypentanoate (25.0 g, 53%) as an oil.

B. Ethyl 5-(3-cyclopentyloxy-4-methoxyphenyl)-3-oxo-4-pentenoate

To a solution of p-toluenesulfonic acid monohydrate (0.13 g, 0.68 mmol) warmed on the steam bath was added ethyl 5-(3-cyclopentyloxy-4-methoxy)-3-oxo-5-hydroxypentanoate (13.5 g, 0.039 mol). After 5 minutes, the solution was cooled and purified by chromatography over flash chromatography silica gel (130 g). Elution with methylene chloride/hexane mixtures gave 3.5 g (27%) of pure ethyl 5-(3-cyclopentyloxy-4-methoxyphenyl)-3-oxo-4-pentenoate.

C. Ethyl 5-(3-cyclopentyloxy-4-methoxyphenyl)-3-oxo-2-ethyoxymethylene-4-pentenoate A solution of ethyl 5-(3-cyclopentyloxy-4-methoxyphenyl) 3-oxo-4-pentenoate (2.2 g, 6.8 mmol) and diethoxymethyl acetate (1.1 g, 6.8 mmol) was heated at 160° for 1 hour. The reaction mixture was taken up in methylene chloride and washed with saturated sodium bicarbonate solution. The methylene chloride was evaporated under reduced pressure and the residue was purified by flash chromatography over 15 g of flash chromatography silica gel. Elution with methylene chloride/hexane mixtures removed some starting material and by-products. Elution with pure methylene chloride afforded 1.1 g (42%) of ethyl 5-(3-cyclopentyloxy-4-methoxyphenyl)-3-oxo-2-ethoxymethylene-4-pentenoate.

D. Ethyl 3-(3-cyclopentyloxy-4-methoxyphenyl-ethyl-2-yl)pyrazole-4-carboxylate

A solution of ethyl 5-(3-cyclopentyloxy-4-methoxyphenyl)-3-oxo-2-ethoxymethylene-4-pentenoate (1.1 g, 2.6 mmol) in ethanol (10 mL) was treated with anhydrous hydrazine (0.1 g, 3.1 mmol) After standing overnight, the solvent was removed under reduced pressure and the residue was purified by flash chromatography over 10 g of flash chromatography silica gel. Elution with methylene chloride afforded the ethyl 3-(3-cyclopentyloxy-4-methoxyphenyl-ethyl-2-yl)pyrazole-4-carboxylate (0.5 g, 54%). Pure title compound mp 97–100° was obtained by crystallization from ether/hexanes.

EXAMPLE 17

3-(3-cyclopentyloxy-4-methoxyphenyl-1-ethen-2-yl) pyrazole-4-methanol

A solution of ethyl 3-(3-cyclopentyloxy-4-methoxyphenyl-1-ethen-2-yl)pyrazole-4-carboxylate (from Example 16), (0.5 g, 1.4 mmol) in THF (50 mL) was stirred overnight with lithium aluminum hydride (0.16 g, 2.1 mmol). The reaction mixture was then treated successively with water, (0.5 mL), 15% aqueous sodium hydroxide (0.5 mL) and water (1.5 mL). The inorganic material was filtered and washed with methylene chloride. The ether and methylene chloride solutions were combined and washed with water and evaporated. The crude product was dissolved in methylene chloride and purified by flash chromatography over 4.5 g of flash chromatography silica gel. Elution with methylene chloride/methanol mixtures afforded 3-(3-cyclopentyloxy-4-methoxyphenyl-1-ethen-2-yl)pyrazole-4-carbinol (030 g, 68%). Pure title compound, mp 121–123°, was obtained by crystallization from toluene.

EXAMPLE 18 ethyl 3-[2-(3-cyclopentyloxy-4-methoxyphenyl) ethyl]pyrazole-4-carboxylate

A solution of ethyl 3-(3-cyclopentyloxy-4-methoxyphenyl-1-ethylene-2-yl)pyrazole-4-carboxylate (Example 16), (1.1 g, 3.1 mmol) in ethyl acetate (50 mL) was hydrogenated at 20 psi over 0.5 g of 10% Pd on carbon catalyst. After 24 hours, the catalyst as filtered and the solution was hydrogenated again with 0.5 g of fresh 10% Pd on carbon catalyst. After hydrogen uptake ceased,the catalyst was filtered and the crude product was purified by flash chromatography over 20 g of flash chromatography silica gel. Elution with methylene chloride and 0.25% ethanol/methylene chloride removed some impurities . Elution with 2% ethanol/methylene chloride afforded ethyl 3-[2-(3-cyclopentyl-oxy-4-methoxyphenyl)ethyl]pryazole-4-carboxylate (0.70 g, 63%) Pure title compound, mp 80–82° was obtained by crystallization from ether/hexanes.

EXAMPLE 19

3-[2-(3-Cyclopentyloxy-4-methoxyphenyl ethyl] pyrazole-4-methanol

A solution of ethyl 3-[2-(3-cyclopentyloxy-4-methoxyphenyl) ethyl]pyrazole-4-carboxylate (from Example 18), (0.40 g, 1.1 mmol) was stirred overnight with lithium aluminum hydride (0.18 g, 4.7 mmol). THF (25 mL) was added and stirring was continued for 1 hour. The reaction mixture was then treated successively with water (0.2 mL), 15% aqueous sodium hydroxide (0.2 mL) and water (0.6 mL). The inorganic material was filtered and washed and methylene chloride. The organic solutions were combined and evaporated under reduced pressure. The crude product was purified by flash chromatography over 3.5 g of flash chromatography silica gel. Elution with methylene chloride and 1% methanol/methylene chloride removed some impurities. Elution with 2% methanol/methylene chloride gave 0.21 g (60%) of 3-[2-(3-cyclopentyloxy-4-methoxyphenyl)ethyl]pyrazole carbinol. Pure title compound, mp 88–91°, was obtained by crystallization from ether/hexanes.

EXAMPLE 20

2-(3-Cyclopentyloxy-4-methoxyphenyl)-4-trifluoromethyl-imidazole 1,1-Dibromo-3,3,3-trifluoroacetone (2.95 g, 1.64 ml, 10.9 mmol) was added to a solution of NaOAc (1.52 g, 18 mmol) in water (8 ml), The solution was heated at 80° C. for 45 min. To the cooled solution at 0° C. was added 3-cyclopentyloxy- 4-methoxybenzaldehyde (2 g, 9.07 mmol) and methanol (34 ml), followed by concentrated NH$_4$OH (11 ml). A homogeneous reaction mixture was obtained, which was stirred overnight at room temperature. Volatiles were removed in vacuo and flash chromatography (SiO$_2$; EtOAc:hexane (3:7)) produced 2-(3-cyclopentyloxy-4-methoxyphenyl)-4-trifluoromethyl imidazole (1.728 g, 58%) as a white solid, mp 157–159° C. $\delta_H$ (250 MHz;CDCl$_3$) 1.45–1.9 (8H,m,4×CH$_2$), 3.85 (3H,s,OMe), 4.7 (1H,m,CH), 6.8 (1H,d,ArH), 7,3 (1H,d,ArH), 7.4 (2H,m,ArH), 10.3 (1H,s,NH)

EXAMPLE 21

2(3Cyclopentyloxy-4-methoxvyhenyl)-imidazole4-carboxylic acid 2-(3-cyclopentyloxy-4-methoxyphenyl)-4-trifluoromethyl imidazole (688 mg, 2.11 mmol) and 1N NaOH (25 ml) were heated at 90° C. for 2 h. Afterwhich time the reaction was made acidic by addition of c.HCl, the precipitate was collected by filtration and the filter was washed with ethanol (5 ml) and ether (5×20 ml), dried in vacuo, to afford 2-(3-cyclopentyloxy-4-methoxyphenyl)-imidazole-4-carboxylic acid (356 mg, 56%) as a light tan solid, mp 206–208° C. $\delta_H$ (250 MHz;d$_4$,MeOH) 1.7 (2H,m,CH$_2$), 1.8–2.0 (6H,m,3×CH$_2$), 3.9 (3H,s,OMe), 4.9 (1H,m,CH), 7.1 (1H,d,ArH), 7.6 (2H,m,ArH), 8.0 (1H,s,ArH).

EXAMPLE 22

2-(3-Cyclopentyloxy-4-methoxyphenyl)-imidazole4formamide

A: 2-(3-Cyclopentyloxy-4-methoxyphenyl)-4-cyanoimidazole

A mixture of 2-(3-cyclopentyloxy-4-methoxyphenyl)-4-trifluoromethyl-imidazole (1.04 g, 3.18 mmol) and 5% aqueous ammonium hydroxide (300 ml) was heated to reflux for 24 hours. The reaction mixture was cooled and carefully neutralised with acetic acid. The mixture was extracted with methylene chloride (3×150 ml) and the volatiles removed in vacuo to afford the crude product. Flash chromatography (SiO$_2$; EtOAc:hexane (2:3)) produced the 2-(3-cyclopentyloxy-4-methoxyphenyl)-4-cyanoimidazole (320 mg, 35%) as a pale yellow solid.

B: 2-(3-Hydroxy-4-methoxyphenyl)-4-imidazole-4-formamide

A mixture of the 2-(3-Cyclopentyloxy-4-methoxyphenyl)-4-cyanoimidazole (320 mg, 1.18 mmol) and c.HCl (25 ml) was heated to 50° C. overnight. The reaction was then cooled to 0° C., neutralised with c.NH$_4$OH and extracted with ethyl acetate (5×80 ml), the combined organics were dried over Na$_2$SO$_4$ and the volatiles removed in vacuo. Flash chromatography (SiO$_2$;CH$_2$Cl$_2$ to CH$_2$Cl$_2$:EtOH (7:3) (1% NH$_3$)) afforded 2-(3-hydroxy-4-methoxyphenyl)-imidazole-4-formamide (110 mg, 40%) as a white solid.

C: 2-(3-Cyclopentylaxy-4-methoxyphenyl)-imidazole-4-formamide

A mixture of 2-(3-hydroxy-4-methoxyphenyl)-imidazole-4-formamide (110 mg, 0.47 mmol), cyclopentyl bromide (60 µl, 0.56 mmol) and K$_2$CO$_3$ (162 mg, 1.2 mmol) in DMF (10 ml) were heated at 70° C. overnight. A further quantity of cyclopentyl bromide (60 µl, 0.56 mmol) and K$_2$CO$_3$ (162 mg, 1.2 mmol) were added and the reaction mixture was cooled to room temperature, diluted with water (50 ml), extracted with ethyl acetate (2×100 ml). The combined organics were washed with brine (30 ml) dried over Na$_2$SO$_4$ and the volatiles removed in vacuo. Flash chromatography (SiO$_2$; CH$_2$Cl$_2$:EtOH (9:1) (1% NH$_3$)) afforded 2-(3-cyclopentyloxy-4-methoxyphenyl)-imidazole-4-formamide (43 mg,) as a white solid, mp d.>195° C.

$\delta_H$ (250 MHz;d$_4$,MeOH) 1.65 (2H,m,CH$_2$), 17–2.0 (6H, m,3×CH$_2$), 3.9 (3H,s,OMe), 7.0 (1H,d,ArH), 7.5 (2H,m, ArH), 7.7 (1H,s,ArH).

EXAMPLE 23

2-(3-Cyclopentyloxy-4-methoxyphenyl)-imidazole-4-carboxylic acid-2,-6-dimethylphenyl amide A mixture of 2-(3-cyclopentyloxy-4-methoxyphenyl)-imidazole-4-carboxylic acid (400 mg, 1.32 mmol) and SOCl$_2$ (10 ml) containing DMF (1 drop) was heated to reflux for 2 hours. The volatiles were removed in vacuo and to the residue was added toluene (25 ml) and the solvent evaporated. This procedure was repeated to remove dissolved gaseous by-products. The residue was dissolved in THF (10 ml) and added dropwise at 0° C. over 10 minutes, to a solution of the salt of 2,6-dimethylaniline (510 µl, 4.14 mmol) in THF (30 ml) (formed by adding a solution of the aniline in THF (15 ml) to a suspension of NaH (167 mg, 4.14 mmol) is THF (15 ml) at room temperature). The resultant solution was stirred at room temperature for 48 hours, diluted with 1N HCl (20 ml) and the mixture extracted with methylene chloride (2×50 ml) The combined organics were dried over Na$_2$SO$_4$ and the volatiles removed in vacuo. Flash chromatography (SiO$_2$; CH$_2$Cl$_2$:EtOH (97:3)) afforded 2-(3-cyclopentyloxy-4-methoxyphenyl)-imidazole-4-carboxylic acid-2,6-dimethylphenyl amide (80 mg, 15%) as a pale yellow solid, mp 118–122° C.

$\delta_H$ (250 MHz;CDCl$_3$) 1.6 (2H,m,CH$_2$), 1.7–2.0 (6H,m, 3×CH$_2$), 2.3 (6H,s,2×Me), 3.9 (3H,s,OMe), 5.0 (1H,m,CH), 6.8 (1H,d,ArH), 7.1 (2H,d,ArH), 7.8–8.0 (3H,m,ArH), 8.5 (1H,6s,NH), 10.3 (1H,6s,NH).

EXAMPLE 24

2-(3-Cyclopentyloxy-4-methoxyphenyl)-imidazole-4-methanol

A: 2-(3-Cyclopentyloxy-4-methoxyphenyl)-imidazole-4-methylcarboxylate

To a solution of 2-(3-cyclopentyloxy-4-methoxyphenyl)-imidazole-4-carboxylic acid (0.5 g, 165 mmol) in dry methanol (2 ml) at 0° C. was added acetyl chloride (0.8 ml, 11.2 mmol) The reaction mixture was stirred at room temperature for 4 days and then the volatiles were removed in vacuo. The oily residue was dissolved in water (20 ml), basified with 1N NaOH and extracted with methylene chloride (3×50 ml) The combined organics were dried over Na$_2$SO$_4$ and the volatiles removed in vacuo. Flash chromatography (SiO$_2$; EtOAc:Hexane (4:1)) afforded 2-(3-cyclopentyloxy-4-methoxyphenyl)-imidazole-4-methyl carboxylate (225 mg, 43%), as a white solid, mp 165–168° C.

B: 2-(3-Cyclopentyloxy-4-methoxyphenyl)-imidazole-4-methanol

To a solution of 2-(3-cyclopentyloxy-4-methoxyphenyl)-imidazole-4-methylcarboxylate (225 mg, 0.71 mmol) in dry THF (15 ml) was added, with stirring at −40° C., a solution of diisobutylaluminium hydride (1M in THF, 6.0 ml, 60 mmol) After 1.5 hours the reaction mixture was poured onto saturated NH$_4$Cl (50 ml) and extracted with ethyl acetate (3×100 ml). The combined organics were washed with saturated NH$_4$Cl (50 ml), dried over Na$_2$SO$_4$ and the volatiles removed in vacuo. Flash chromatography (SiO$_2$; CH$_2$Cl$_2$:EtOH (95:5) (1% NH$_3$)) afforded 2(3-cyclopentyloxy-4-methoxyphenyl)-imidazole-4-methanol (88 mg, 45%) as a white solid, mp 188–190° C.

$\delta_H$ (250 MHz;CDCl$_3$) 1.5 (2H,m,CH$_2$), 1.6–1.9 (6H,m, 3×CH$_2$), 3.7 (3H,s,OMe), 4.5 (2H,s,CH$_2$O), 4.7 (1H,,m, CH), 6.7 (1H,d,ArH), 6.8 (1H,s,ArH), 7.3 (1H,dd,ArH), 7.4 (1H,d,ArH).

EXAMPLE 25

2-(3Cyclopentloxy-4methoxyphenyl)-imidazole-4-carboxylic acid, N-(2hydroxyethyl)amide To a solution of 2-(3-Cyclopentyloxy-4-methoxyphenyl)-imidazole-4-carboxylic acid (500 mg, 1.65 mmol) in DMF (15 ml) at room temperature was added carbonyldiimidazole (295 mg, 1.8 mmol). The resultant solution was stirred for 30 minutes and then ethanolamine (180 μl, 1.8 mmol) was added and the reaction mixture stirred at room temperature overnight. Water (75 ml) was added and the mixture extracted with ethyl acetate (2×75 ml). The combined organics were washed with brine (40 ml), dried over Na$_2$SO$_4$ and the volatiles removed in vacuo. Flash chromatography (SiO$_2$; CH$_2$Cl$_2$:EtOH (95:5) (1% NH$_3$)) afforded 2-(3-cyclopentyloxy-4-methoxyphenyl)-imidazole-4-carboxylic acid, N-(2-hydroxyethyl) amide (247 mg, 43%) as a white solid, mp 206–208° C.

$\delta_H$ (250 MHz;d$_6$,DMSO) 1.6 (2H,m,CH$_2$), 1.65 (4H,m, CH$_2$), 1.9 (2H,m,CH$_2$), 3.3 (2H,m,NCH$_2$), 3.3 (1H,s,NH), 3.5 (2H,m,OCH$_2$), 3.8 (3H,s,OMe), 4.8 (1H,m,CH), 4.8 (1H,s,OH), 7.0 (1H,d,ArH), 7.5 (1H,d,ArH), 7.7 (1H,s,ArH), 7.85 (1H,t,ArH), 12.8 (1H,6s,NH).

EXAMPLE 26

4-(1-(3-Cyclopentyloxv-4-methoxyphenyl)-2-phenyl-ethyl)-5-methylpyrazol-3-one

A: Ethyl-3(3-Cyclopentyloxy-4-methoxyphenyl)-2-acetyl-prop-2-enoate

A mixture of 3-Cyclopentyloxy-4-methoxybenzaldehyde (7 g, 31.8 mmol), ethyl acetoacetate (4.13 g, 31.8 mmol), piperidine (275 mg, 3.18 mmol) and glacial acetic acid (100 mg) in toluene (350 ml) was heated at reflux with a Dean-Stark trap for 2 days, during which time, at regular intervals, further additions of piperidine (4×275 mg) and glacial acetic acid (4×100 mg) were made. The reaction mixture was then diluted with water and extracted with methylene chloride (3×150 ml), dried over Na$_2$SO$_4$ and the volatiles removed in vacuo. Flash chromatography (SiO$_2$; EtOAc:hexane (1:9)) affordedethyl-3-(3-cyclopentyloxy-4-methoxyphenyl)-2-acetyl-prop-2-enoate (2 g, 19%) as a yellow oil.

B: Ethyl-3-(3-Cyclopentyloxy-4-methoxyphenyl)-2-acetyl-4-phenylbutanoate

Cuprous iodide (1.15 g, 6.05 mmol) in dry THF (10 ml) was treated at 0° C. with benzylmagnesium bromide (2M in THF, 6.05 ml, 12.1 mmol) over a 3 minute period. The cuprate was stirred at 0° C. for 30 minutes and then cooled to −78° C. and then TMSCl (3.28 g, 30.2 mmol) in THF (5 ml) was added dropwise keeping the reaction temperature below −60° C. The mixture was stirred at below −60° C. for a further 10 minutes and then ethyl-3-(3-cyclopentyloxy-4-methoxyphenyl)-2-acetyl-prop-2-enoate (1 g, 3.01 mmol) in THF (5 ml) was added dropwise over 3 minutes. The mixture was stirred at below −60° C. for 45 minutes and then saturated NH$_4$Cl (30 ml) and water (20 ml) were added. The mixture was allowed to warm to room temperature, the resultant precipitate was removed by filtration and the filtrate evaporated, the residue was dissolved in methylene chloride (200 ml), washed with water (30 ml), In HCl (50 ml) and water (30 ml), dried over Na$_2$SO, and the volatiles removed in vacuo. Flash chromatography (SiO$_2$; EtOAc:hexane (1.9)) afforded ethyl-3-(3-cyclopentyloxy-4-methoxyphenyl)-2-acetyl-4-phenyl-butanoate (1.19 g, 92%) as a yellow oil.

C: 4-(1-(3-Cyclopentyloxy-4-methoxvphenyl))-2-phenyl-ethyl)-5-methyl-pyrazol-3-one Hydrazine monohydrate (207 mg, 4.2 mmol) was added to a solution of3-ethyl-(3-cyclopentyloxy-4-methoxyphenyl)-2-acetyl-4-phenyl-butanoate (1.186 g, 2.8 mmol) in methanol at 0° C. The resultant mixture was allowed to reach room temperature over 45 minutes and then heated to reflux overnight. The volatiles were removed in vacuo and flash chromatography (SiO$_2$; CH$_2$Cl$_2$:EtOH (95:5) (1% NH$_3$)) afforded 4-(1-(3-cyclopentyloxy-4-methoxyphenyl)-2-phenyl-ethyl)-5-methyl-pyrazol-3-one (460 mg, 42%) as a pale yellow solid, mp 88–90° C.

$\delta_H$ (250 MHz;CDCl$_3$) 1.5 (2H,m,CH$_2$), 1.6–1.9 (6H,m, 3×CH$_2$), 1.9 (3H,s,Me), 3.2–3.5 (2H,m,ArCH$_2$), 3.8 (3H,s, OMe), 3.85 (1H,m,ArCH), 4.7 (1H,m,CH), 6.7 (1H,d,ArH), 6.85 (1H,dd,ArH), 7.0 (1H,d,ArH), 7.2 (5H,m,ArH).

EXAMPLE 27

Protocols for PDE IV, PDE III, and PDE V inhibition activity are set forth below:

Type III Phosphodiesterase Enzyme Isolation Protocol

The Type III PDE is isolated from human platelets using a procedure similar to that previously described by Weishaar, R. E.; Burrows, S. D.; Kobylarg, D. C., Quade, N. M.; Evans, D. B., Biochem. Pharmacol., 35:787, 1986. Briefly, 1–2 units of platelets are suspended in an equal volume of buffer (20 mM Tris-HCl, pH 7.5, containing 2 mM magnesium acetate, 1 mM dithiothreitol, and 5 mM Na$_2$ EDTA) The proteinase inhibitor phenylmethyl-sulfonyl fluoride (PMSF) is also included in this buffer at a final concentration of 200 μM. The suspension is homogenized using a polytron and the homogenate centrifuged at 100, 000×g for 60 minutes. This and all subsequent procedures are performed at 0–4° C. The supernatant is then filtered through four layers of gauze and applied to a DEAE-Trisacryl M column, previously equilibrated with buffer B (20 mM Tris-HCl, pH 7.5, containing 1 mM magnesium acetate, 1 mM dithiothreitol and 200 μM PMSF). After application of the sample, the column is washed with several bed volumes of buffer B, after which the different forms of PDE are eluted from the column using two successive linear NaCl gradients (0.05–0.15M, 300 ml total; 0.15–0.40M, 200 ml total). Five ml fractions are collected and assayed for cyclic AMP and cyclic GMP PDE activity. Fractions containing PDE III activity are pooled and dialyzed overnight against 4 L of buffer B. The dialyzed PDE III is then concentrated to 10% of the original volume, diluted to 50% with ethylene glycol monoethyl ether and stored at −20° C. PDE III can typically be retained for up to four weeks with little or no loss of activity.

Measuring Type III PDE Activity

Enzyme activity is assessed by measuring the hydrolysis of [$^3$H]-cyclic AMP, as described by Thompson, W. J ., Teraski, W. L., Epstein, P. N., Strada, S. J.: Adv. Cyclic Nucleotide Res. 10:69, 1979. The cyclic AMP concentration used in this assay is 0.2 μM, which approximates to the K$_m$ value. Protein concentration is adjusted to ensure that no more than 15% of the available substrate is hydrolyzed during the incubation period.

All test compounds are dissolved in dimethyl sulfoxide (final concentration of 2.5%). This concentration of dimethyl sulfoxide inhibits enzyme activity by approximately 10%.

Type IV Phosphodiesterase Enzyme Isolation Protocol

The Type IV PDE is isolated from bovine tracheal smooth muscle using a procedure similar to that previously described by Silver, P. J., Hamel, L. T., Perrone, M. H. Bentley, R. G. Bushover, C. R., Evans, D. B.: Eur. J. Pharmacol. 150:85,1988.(1). Briefly, smooth muscle from bovine trachea is minced and homogenized using a polytron in 10 volumes of an extraction buffer containing 10 mM Trisacetate (pH 7.5), 2 mM magnesium chloride, 1 mM dithiothreitol and 2,000 units/ml of aprotinin. This and all subsequent procedures are performed at 0–4° C. The homogenate is sonicated and then centrifuged at 48,000×g for 30 minutes. The resulting supernatant is applied to a DEAE Trisacryl M column previously equilibrated with sodium acetate and dithiothreitol. After applications of the sample, the column is washed with sodium acetate/dithiothreitol, after which the different forms of PDE are eluted from the column using a linear Tris-HCl/NaCl gradient. Fractions containing Type IV PDE are collected, dialyzed and concentrated to 14% of the original volume. The concentrated fractions are diluted to 50% with ethylene glycol and stored at −20° C.

Measuring Type IV PDE Activity

Enzyme activity is assessed by measuring the hydrolysis of [$^3$H]-Epstic AMP, as described by Thompson, W. J., Teraski, W. L., Epstein, P. N., Strada, S. J.: Adv. Cyclic Nucleotide Res. 10,69, 1979. The cyclic AMP concentration used in this assay is 0.2 μM, which approximates to the $K_m$ value. Protein concentration is adjusted to ensure that no more than 15% of the available substrate is hydrolyzed during the incubation period.

All test compounds are dissolved in dimethyl sulfoxide (final concentration of 2.5%). This concentration of dimethyl sulfoxide inhibits enzyme activity by approximately 10%.

Type V Phosphodiesterase Enzyme Isolation Protocol

Enzyme Isolation Procedure

The Type V PDE is isolated using a procedure similar to that previously described by Weishaar et al. (Weishaar, R. E., Kobylarz-Singer, D. C., Keiser, J., Haleen, S. J., Major, T. C., Rapundalo, S., Peterson, J. T., Panek, R.: Hypertension 15:528, 1990). Briefly, 1–2 units of platelets are suspended in an equal volume of buffer A (20 mM Tris-HCl, pH 7.5, containing 2 mM magnesium acetate, 1 mM dithiothreitol, and 5 mM Na$_2$EDTA) using a polytron. The proteinase inhibitor phenylmethylsulfonyl fluoride (PMSF) are also included in this buffer at a final concentration of 200 μM. This and all subsequent procedures are performed at 0–4° C. The homogenate is then centrifuges at 100,000×g for 60 minutes. The supernatant is then removed and filtered through four layers of gauze and applied to a DEAE-Trisacryl M column. The column is washed with several bed volumes of buffer B (20 mM Tris-HCl$_1$, pH 7.5, containing 2 mM magnesium acetate, 1 mM diothiothreitol, and 200 μM PMSF) and eluted by two successive linear NaCl gradients (0.05–0.15M, 300 ml total; 0.15–0.40M, 200 ml total). Five ml fractions are collected and assayed for cyclic AMP and cyclic GMP PDE activity. Fractions that contain PDE V are pooled and dialyzed overnight against 4 L of buffer C (20 mM Tris-HCl, pH 7.5, containing 2 mM magnesium acetate and proteinase inhibitors) The dialyzed PDE V is then concentrated to 10% of the original volume, diluted to 50% with ethylene glycol monoethyl ether and stored at −20° C. PDE V can typically be retained for up to four weeks with little or no loss of activity.

Measuring Type V PDE Activity

Enzyme activity are assessed by measuring the hydrolysis of [$^3$H]-cyclic GMP, as described by Thompson et al. (Thompson, W. J., Teraski, W. L., Epstein, P. N., Strada, S. J.: Adv. Cyclic Nucleotide Res. 10:69, 1979). The cyclic GMP concentration used in this assay is 0.2 μM, which approximates to the $K_m$ value. Protein concentration is adjusted to ensure that no more than 15% of the available substrate is hydrolyzed during the incubation period.

All test compounds are dissolved in dimethyl sulfoxide (final concentration of 2.5%). This concentration of dimethyl sulfoxide inhibits enzyme activity by approximately 10%. The reference Type V PDE inhibitor zaprinast is evaluated with each assay.

The compounds are tested over concentration range 0.1, 1, 10, 100 μM (n=1), and $I_{50}$ determinations are made using 5 appropriate concentrations (n=2).

EXAMPLE 28

Following the above procedures, the PDE III, PDE IV, PDE V inhibition for the compound of Example 1, 3-(3-cyclopentyloxy-4-methoxybenzylamino)-4-hydroxymethylpyrazole, and rolipram (PDE III, PDE IV) are tested and compared. The results are shown in Tables 1–3 below:

TABLE 1

PDE III ACTIVITY

| Compound | Molecular Weight | % Inhibition | | | |
|---|---|---|---|---|---|
| | | 1.0 μM | 10 μM | 100 μM | 300 μM |
| Ex. 1 | 317.4 | 8% | 22% | 53% | precipitate |
| Rolipram | — | — | 7% | 18% | 35% |

TABLE 2

PDE IV ACTIVITY

| Example | Molecular Mol. Wt. | % Inhibition | | | | |
|---|---|---|---|---|---|---|
| | | 0.001 μM | 0.003. μM | 0.01 μM | 0.03 μM | 0.1 μM |
| Ex. 1 | 317.4 | 10% | 26% | 42% | 58% | 70% |
| Example | | 1.0 μM | | 10 μM | | |
| Rolipram | | 36% | | 67% | | |

TABLE 3

PDE V ACTIVITY

| Compound | Molecular Weight | PDE - % Inhibition | | | |
|---|---|---|---|---|---|
| | | 0.1 μM | 1 μM | 10 μM | 100 μM |
| Example 1 | 317.40 | 0 | 0 | 4 | 30# |

The concentration of Example 1 which yielded 50% inhibition of PDE IV (IC$_{50}$) was 0.016 μM.

The concentration of rolipram which yielded 50% inhibition of PDE IV (IC$_{50}$) in this same assay was 4.5 μM.

EXAMPLE 29

In this Example, the compounds prepared in the above examples were prepared as set forth above and tested for Type III and Type IV PDE Activity in similar fashion as set forth with regard to the procedures set forth in Example 20. The results are set forth in Table 4 below:

TABLE 4

| EXAMPLE | ACTIVITIES | |
|---|---|---|
| | PDE IV IC$_{50}$ ($\mu$M) | PDE III IC$_{50}$ ($\mu$M) |
| 1 | 0.016 | >100 |
| 2 | 53 | >300 |
| 3 | 109 | >300 |
| 4 | 4.4 | >300 |
| 5 | 15 | >100 |
| 6 | 20% @ 100 $\mu$M | >100 |
| 7 | 19% @ 100 $\mu$M | >100 |
| 8 | 25 | 46 |
| 9 | 13 | >100 |
| 10 | 7.8 | >300 |
| 11 | 78 | >300 |
| 12 | 3.593 | 85.317 |
| 13 | 22.80 | >100 |
| 14 | 7.30 | >300 |
| 15 | 0.17 | >300 |
| 16 | 1.47 | 7.320 |
| 17 | 8.00 | >100 |
| 18 | 12.50 | >100 |
| 19 | 17.508 | >300 |
| 20 | 14.68 | >100 |
| 21 | 7.44 | >250 |
| 22 | 3.9 | 76 |
| 23 | 7.28 | >200 |
| 24 | 17.54 | >300 |
| 25 | 4.48 | >250 |
| 26 | 2.80 | >100 |

As can be seen from the foregoing, the inventive compounds provide high levels of PDE-IV inhibition while at the same time relatively low levels of PDE-III inhibition.

While the invention has been illustrated with respect to the production and use of a particular compound, it is apparent that variations and modifications of the invention can be made without departing from the spirit or scope of the invention.

What is claimed is:

1. A compound of the formula:

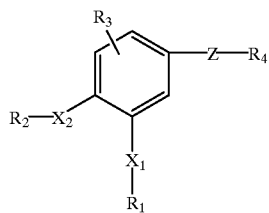

wherein:
X$_1$ and X$_2$ are the same or different and each is O or S;
R$_1$ and R$_2$ are the same or different and each is selected from the group consisting of a straight-chain or branched alkyl or alkenyl containing from 1 to 12 carbon atoms, cycloalkyl and cycloalkyl-alkyl group containing from 3 to 7 carbon atoms in the cycloalkl moiety; or one of R$_1$ and R$_2$ is hydrogen and the other is selected from the group consisting of a straight-chain or branched alkyl or alkenyl containing from 1 to 12 carbon atoms, cycloalkyl and cycloalkyl-alkyl group containing from 3 to 7 carbon atoms in the cycloalkyl moiety;

R$_3$ is hydrogen, halogen, or a straight-chain or branched alkyl or alkenyl group containing from 1 to 12 carbon atoms, a cycloalkyl or cycloalkyl-alkyl group containing from 3 to 7 carbon atoms in the cycloalkyl moiety;

Z is a linkage selected form —CH$_2$O—, —CH$_2$CH$_2$—, —CH$_2$NH—, CH$_2$N(Me), —NHCH$_2$—, CH$_2$CONH—, —NHCH$_2$CO—, CH$_2$CO—COCH$_2$—, —CH$_2$COCH$_2$—,CH(CH$_3$)—, —CH=, and —HC=CH—, wherein the carbon and/or nitrogen atoms are optionally substituted with a lower alkyl, halogen, hydroxy or alkoxy group, R$_4$ is pyrazole or pyrazolone, which is optional substituted with one or more halogen atoms, C$_{1-4}$ alkyl groups, hydroxyl groups, cyano groups, nitro groups, carboxyl groups, C$_{1-4}$ alkyl esters, alkoxy groups, alkoxycarbonyl, amido, carboxamido, optionally substituted amino groups, cycloalkyl and cycloalkyl-alkyl groups containing from 3 to 7 carbon atoms in the cycloalkyl moiety, or aryl or aralkyl groups containing from 6 to 10 carbon atoms; said alkyl, cycloalkyl, cycloalkyl-alkyl, aryl, and aryl-alkyl groups being optionally substituted by halogen atoms, hydroxyl groups, cyano groups, carboxyl groups, C$_{1-4}$ alkoxy groups, alkoxycarbonyl, carboxamido or optionally substituted amino groups, or one or more lower akyl groups having from 1 to 3 carbon atoms, with the proviso that said pyrazole or pyrazolone is not substituted on a nitrogen atom with aryl or aralkyl.

2. The compound of claim 1 wherein R$_1$ is alkyl of 1–12 carbon atoms or cycloalkyl of 3–6 carbon atoms, which cycloalkyl is optionally substituted by one or more alkyl groups or by one or more halogens, R$_2$ is hydrogen, or alkyl of 1–12 carbon atoms, and wherein R$_3$ is hydrogen, lower alkyl or halogen.

3. The compound of claim 2 wherein R$_2$ is lower alkyl.

4. The compound of claim 3 wherein R$_1$ is cycloalkyl optionally substituted by one or more halogens.

5. The compound of claim 1 wherein R$_2$ is methyl or ethyl and wherein R$_1$ is cyclopentyl optionally substituted by a straight-chain lower alkyl or alkenyl group containing from about 1 to about 6 carbon atoms, optionally substituted with one or more halogen atoms, hydroxyl groups, cyano groups, nitro groups, carboxyl groups, alkoxy groups, alkoxycarbonyl, carboxamido or optionally substituted amino groups.

6. The compound of claim 2 wherein Z is a linkage selected from —CH$_2$CH$_2$—, —CH$_2$NH—, CH$_2$N(Me), —NHCH$_2$—, —CH$_2$CONH—, and —NHCH$_2$CO—.

7. The compound of claim 2, wherein X$_1$ and X$_2$ are O.

8. The compound of claim 6 wherein R$_4$ is a pyrazole substituted at the 4-position with a lower alkyl having from about 1 to about 3 carbon atoms.

9. The compound of claim 6 wherein Z is —CH$_2$NH—.

10. The compound of claim 6 wherein Z is —CH$_2$NH— and R$_4$ is a pyrazole substituted at the 4-position with a lower alkyl having from about 1 to about 3 carbon atoms.

11. The compound of claim 1, selected from the group consisting of
3-(3-cyclopenytyloxy-4-methoxybenzyalmino)4-hydoxymethyl pyrazole;
3-(3-cyclopenytyloxy-4-methoxybenzyalmino)-4-methoxymethylpyrazole;
3-(3-cyclopenytyloxy-4-methoxybenzyalmino)-4-pyrazolecarboxamide;
3-(3-cyclopenytyloxy-4-methoxybenzylamino) pyrazole;
3-(3-cyclopenytyloxy-4-methoxybenzylamino)-4-pyrazolecarboxylic acid;

[4-(3-cyclopenytyloxy-4-methoxybenzyl)-5-methyl-pyrazol-3-one;]

4-[1-(3-cyclopenytyloxy-4-methoxy-phenyl)ethyl]-5-methyl-pyrazol-3-one;

ethyl 3-(3cyclopenytyloxy-4-methoxybenzylamino)-pyrazole-4-carboxylate;

3-(3-cyclopenytyloxy-4-methoxybenzylamino)-4-methylpyrazole;

ethyl 3(3-cyclopenytyloxy-4-methoxyphenyl-1-ethen-2-yl)-pyrazole-4carboxylate;

3-(3-cyclopenytyloxy-4-methoxyphenyl-1-ethen-2-yl)-pyrazole-4-methanol;

ethyl 3(2-(3-cyclopenytyloxy-4methoxyphenyl)ethyl)-pyrazole-4-carboxylate;

3-(2-(3-cyclopenytyloxy-4methoxyphenyl)ethyl)-pyrazole-4-methanol; and 4-(1-(3-cyclopenytyloxy-4-metoxyphenyl)2-phenyl-ethyl)5-methyl-pyrazole-3-one.

12. A compound of the formula:

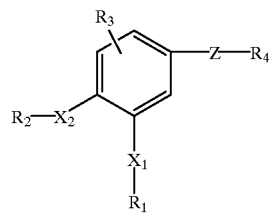

wherein:

$X_1$ and $X_2$ are the same or different and each is O or S;

$R_1$ and $R_2$ are the same or different and each is selected from the group consisting of a straight-chain or branched alkyl or alkenyl containing from 1 to 12 carbon atoms, cycloalkyl and cycloalkyl-alkyl group containing from 3 to 7 carbon atoms in the cycloalkyl moiety; or one of $R_1$ and $R_2$ is hydrogen and the other is selected from the group consisting of a straight-chain or branched alkyl or alkenyl containing from 1 to 12 carbon atoms, cycloalkyl and cycloalkyl-alkyl group containing from 3 to 7 carbon atoms in the cycloalkyl moiety;

$R_3$ is hydrogen, halogen, or a straight-chain or branched alkyl or alkenyl group containing from 1 to 12 carbon atoms, a cycloalkyl or cycloalkyl-alkyl group containing from 3 to 7 carbon atoms in the cycloakyl moiety;

Z is a linkage selected from —CH$_2$O—, CH$_2$CH$_2$—, —CH$_2$NH—, —CH$_2$N(Me)—, —NHCH$_2$—, —CH$_2$CONH—, —NHCH$_2$CO—, —CH$_2$CO—, —COCH$_2$—, —CH$_2$COCH$_2$—, —CH(CH$_3$)—, —CH=, and —HC=CH—, wherein the carbon and/or nitrogen atoms are optionally substituted with a lower alkyl, halogen, hydroxy or alkoxy group;

$R_4$ is pyrazole or pyrazolone, which is optionally substituted only on its carbon atoms with one or more halogen atoms, $C_{1-4}$ alkyl groups, hydroxyl groups, cyano groups, nitro groups, carboxyl groups, $C_{1-4}$ alkyl esters, alkoxy groups, alkoxycarbonyl, amido, carboxamido, substituted or unsubstituted amino groups, cycloalkyl or cykloalkyl-alkyl groups containing from 3 to 7 carbon atoms in the cycloalkyl moiety, or aryl or aralkyl groups containing from 6 to 10 carbon atoms; said alkyl, cycloalkyl, cycloalkyl-alkyl, aryl, and aryl-alkyl groups being optionally substituted by halogen atoms, hydroxyl groups, cyano groups, carboxyl groups, $C_{1-4}$ alkoxy groups, alkoxycarbonyl, carboxamido or optionally substituted amino groups, or one or more lower alkyl groups having from 1 to 3 carbon atoms.

13. A compound of the formula:

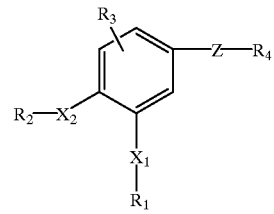

wherein:

$X_1$ and $X_2$ are the same or different and each is O or S;

$R_1$ and $R_2$ are the same or different and each is selected from the group consisting of a straight-chain or branched alkyl or alkenyl containing from 1 to 12 carbon atoms cycloalkyl and cycloalkyl-alkyl group containing from 3 to 7 carbon atoms in the cycloalkyl moiety, or one of $R_1$ and $R_2$ is hydrogen and the other is selected from the group consisting of a straight-chain or branched alkyl or alkenyl containing from 1 to 12 carbon atoms, cycloalkyl and cycloalkyl-alkyl group containing from 3 to 7 carbon atoms in the cycloalkyl moiety ;

$R_3$ is hydrogen, halogen, or a straight-chain or branched alkyl or alkenyl group containing from 1 to 12 carbon atoms, a cycloalkyl or cycloalkyl-alkyl group containing from 3 to 7 carbon atoms in the cycloalkyl moiety;

Z is a linkage selected from —CH$_2$O—, —CH$_2$CH$_2$—, CH$_2$NH—, CH$_2$N(Me)—, —NHCH$_2$—, —CH$_2$CONH—, —NHCH$_2$CO—, —CH$_2$CO—, —COCH$_2$—, —CH$_2$COCH$_2$—, —CH=, and —HC=CH—, wherein the carbon and/or nitrogen atom are optionally substituted with a lower alkyl, halogen, hydroxy or alkoxy group;

$R_4$ is pyrazole or pyrazolone, which is optionally substituted with one or more halogen atoms, $C_{1-4}$ alkyl groups, hydroxyl groups, cyano groups, nitro groups, carboxyl groups, $C_{1-4}$ alkyl esters, alkoxy groups, alkoxycarbonyl, amido, carboxamido, optionally substituted amino groups, cycloalkyl and cycloalkyl-alkyl groups containing from 3 to 7 carbon atoms in the cycloalkyl moiety, or akyl or aralkyl groups containing from 6 to 10 carbon atoms; said alkyl, cycloalkyl, cycloalkyl-alkyl, aryl, and aryl-alkyl groups being optionally substituted by halogen atoms, hydroxyl groups, cyano groups, carboxyl groups, $C_{1-4}$ alkoxy groups, alkoxycarbonyl, carboxamido or optionally substituted amino groups, or one or more lower alkyl groups having from 1 to 3 carbon atoms, provided that when $R^4$ is substituted with aryl Z is not —CH$_2$NH—, —CH$_2$N(Me)— or —NHCH$_2$—.

14. A compound of the formula:

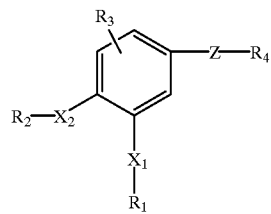

wherein:

X₁ and X₂ are the same or different and each is O or S;

R₁ and R₂ are the same or different and each is selected from the group consisting of a straight-chain or branched alkyl or alkenyl containing from 1 to 12 carbon atoms, cycloalkyl and cycloalkyl-alkyl group containing from 3 to 7 carbon atoms in the cycloalkyl moiety; or one of R₁ and R₂ is hydrogen and the other is selected from the group consisting of a straight-chain or branched alkyl or alkenyl containing from 1 to 12 carbon atoms, cycloalkyl and cycloalkyl-alkyl group containing from 3 to 7 carbon atoms in the cycloalkyl moiety;

R₃ is hydrogen, halogen, or a straight-chain or branched alkyl or alkenyl group containing from 1 to 12 carbon atoms, a cycloalkyl or cycloalkyl-alkyl group containing from 3 to 7 carbon atoms in the cycloalkyl moiety;

Z is a linkage selected from —CH₂O—, CH₂CH₂—, —CH₂NH—, —CH₂N(Me)—, —NHCH₂—, CH₂CONH—, —NHCH₂CO—,—CH₂CO—, —COCH₂—, —CH₂COCH₂—, —CH(CH₃)—, —CH=, and —HC=CH—, wherein the carbon and/or nitrogen atoms are optionally substituted with a lower alkyl, halogen, hydroxy or alkoxy group;

R₄ is pyrazole or pyrazolone, which is optionally substituted with one or more halogen atoms, C₁₋₄ alkyl groups, hydroxyl groups, cyano groups, nitro groups, carboxyl groups, C₁₋₄ alkyl esters, alkoxy groups, alkoxycarbonyl, amido, carboxamido, optionally substituted amino groups, or cycloalkyl and cycloalkyl-alkyl groups containing from 3 to 7 carbon atoms in the cycloalkyl moiety; said alkyl, cycloalkyl and cycloalkyl-alkyl groups being optionally substituted by halogen atoms, hydroxyl groups, cyano groups, carboxyl groups, C₁₋₄ alkoxy groups, alkoxycarbonyl, carboxamido or optionally substituted amino groups, or one or more lower alkyl groups having from 1 to 3 carbon atoms.

15. A compound of the formula:

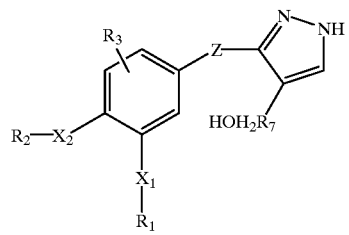

wherein:

X₁ and X₂ are the same or different and each is O or S;

R₁ is an alkyl of 1–12 carbon atoms or a cycloalkyl of 3–6 carbon atoms, which cycloalkyl is optionally substituted by one or more alkyl groups or by one or more halogens;

R₂ is hydrogen or alkyl of 1–12 carbon atoms;

R₃ is hydrogen, lower alkyl or halogen;

Z is a linkage selected from —CH₂—, —CH₂CH₂—, —CH₂NH—, —NHCH₂—, —CH₂N(Me)—, —CH₂CONH—, —NHCH₂CO—, —CH₂CO—, —COCH₂—, —CH₂COCH₂—, —CH(CH₃)—, —CH=, and —HC=CH—;

and R₇ is —C or —CH₂C.

16. The compound of claim 15, wherein X₁ and X₂ are O.

17. The compound according to claim 16, wherein R₂ is methyl or ethyl and wherein R₁ is cyclopentyl.

18. The compound of claim 15, wherein Z is —CH₂NH—.

19. A pharmaceutical composition comprising a compound having the chemical structure set forth in claim 1 and a pharmaceutically acceptable carrier.

20. The pharmaceutical composition of claim 19, selected from the group consisting of 3- (3-cyclopentyloxy-4-methoxybenzy-lamino)-4-hydroxymethyl pyrazole and 3-(3-cyclopentyloxy-4-methoxybenzylamino)-4-methoxymethylpyrazole.

21. A method of effecting selective PDE IV inhibition in a patient requiring the same, which comprises administering an effective amount of the compound of claim 1.

22. The method of claim 21, wherein said compound is selected from the group consisting of 3-(3-cyclopentyloxy-4-methoxybenzylamino)-4-hydroxymethyl pyrazole and 3-(3-cyclopentyloxy-4-methoxybenzylamino)-4-methoxymethylpyrazole.

23. A method of treating a mammal suffering from a disease state selected from thd group consisting of asthma, allergies, inflammation, depression, dementia, atopic diseases, rhinitis and disease states associated with abnormally high physiological levels of cytokine, comprising administering an effective amount of the compound of claim 1 or claim 15.

24. The method of claim 23, wherein said compound is selected from the group consisting of 3-(3-cyclopentyloxy-4-methoxybenzylamino)-4-hydroxymethyl pyrazole and 3-(3-cyclopentyloxy-4-methoxybenzylamino)-4-methoxymethylpyrazole.

* * * * *